United States Patent [19]

O'Donnell et al.

[11] Patent Number: 5,453,575
[45] Date of Patent: Sep. 26, 1995

[54] APPARATUS AND METHOD FOR DETECTING BLOOD FLOW IN INTRAVASCULAR ULTRASONIC IMAGING

[75] Inventors: Matthew O'Donnell, Ann Arbor, Mich.; Michael J. Eberle, Fair Oaks, Calif.; Douglas N. Stephens, Davis, Calif.; Gerald L. Litzza, Sacramento, Calif.; Daniel S. Haviland, Citrus Heights, Calif.

[73] Assignee: Endosonics Corporation, Rancho Cordova, Calif.

[21] Appl. No.: 234,848

[22] Filed: Apr. 28, 1994

Related U.S. Application Data

[63] Continuation-in-part of Ser. No. 12,251, Feb. 1, 1993, Pat. No. 5,368,037.

[51] Int. Cl.$^6$ ........................................ A61B 8/12
[52] U.S. Cl. ........................ 128/662.06; 128/661.01
[58] Field of Search .................. 128/660.03, 660.07, 128/661.01, 661.07–661.10, 662.06; 606/159

[56] References Cited

U.S. PATENT DOCUMENTS

| | | | |
|---|---|---|---|
| 4,821,731 | 4/1989 | Martinelli et al. | 128/660.03 |
| 5,183,048 | 2/1993 | Eberle | 128/661.01 |
| 5,186,177 | 2/1993 | O'Donnell et al. | 128/662.06 |
| 5,199,437 | 4/1993 | Langberg | 128/662.06 |
| 5,226,847 | 7/1993 | Thomas, III et al. | 128/662.06 |
| 5,257,629 | 11/1993 | Kitney et al. | 128/662.06 |
| 5,273,045 | 12/1993 | Chihara et al. | 129/662.06 |
| 5,327,894 | 7/1994 | Thomas | 128/661.09 |

OTHER PUBLICATIONS

"Discrimination Of The Intravascular Lumen And Dissections In A Single 30-MHz US Image: Use of 'Confounding' Blood Backscatter To Advantage", by Gerard Pasterkamp, et al., *Radiology*, Jun. 1993, vol. 187, No. 3, pp. 871–872.

*Primary Examiner*—Francis Jaworski
*Attorney, Agent, or Firm*—Leydig, Voit & Mayer, Ltd.

[57] ABSTRACT

An apparatus and method are described for imaging blood flow from within a vasculature. An ultrasound catheter probe carrying an ultrasound transducer array is inserted within a blood vessel. The transducer array emits ultrasound excitation signals and receives ultrasound echo waveforms reflected from blood and tissue in a region of the vasculature. A series of the echo waveforms resulting from a series of excitation signals are combined in a manner such that the echo signals from static features in the region, such as tissue and plaque, are significantly attenuated. The combined signal primarily represents the relatively dynamic features in the region (i.e. the blood flow). A blood flow image is constructed from the combined signal. The blood flow image is colorized and combined with an image of the relatively static features in the region. Thereafter, the combined image is displayed on a video display.

41 Claims, 17 Drawing Sheets

APPARATUS AND METHOD FOR DETECTING BLOOD FLOW IN INTRAVASCULAR ULTRASONIC IMAGING

This application is a continuation-in-part of U.S. application Ser. No. 08/012,251, filed Feb. 1, 1993, now U.S. Pat. No. 5,368,037, issued Nov. 29, 1994.

FIELD OF THE INVENTION

This invention relates to ultrasound imaging apparatuses placed within a cavity to provide images thereof, and more specifically, to ultrasound imaging apparatuses and methods for providing images of a cavity comprising static and dynamic regions.

BACKGROUND OF THE INVENTION

In the United States and many other countries, heart disease is the leading cause of death and disability. One particular kind of heart disease is atherosclerosis, which involves the degeneration of the walls and lumen of the artery walls throughout the body. Scientific studies have demonstrated the thickening of the arterial wall and eventual encroachment of the tissue into the lumen as fatty material is built up. This material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart muscles. If blood flow to the heart muscle is significantly reduced or cut off, a myocardial infarction or "heart attack" often occurs. If not treated in sufficient time, a heart attack frequently leads to death.

The medical profession relies upon a wide variety of tools to treat coronary disease, ranging from drugs to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to restore blood flow.

The practiced method for guiding a catheter during the performance of procedures such as PTCA has been to use real time X-ray images. With this method, a radiopaque dye is injected into the coronary tree in order to provide a map of blood flow. This technique facilitates identification by a physician of sites where blood flow is restricted. After identifying the sites, therapeutic devices are positioned using a live X-ray image for guidance in order to treat the lesion(s). However, the X-ray image does not give information about the morphology, i.e., form and structure, of the artery.

In the last 5 years, cardiologists have adopted a new technique to obtain information about the coronary vessel and to help view the effects of the therapy on the form and structure of the vessel and not just the blood flow. This technique, known as Intracoronary or Intravascular Ultrasound (ICUS/IVUS) employs miniaturized transducers on the tip of the catheter which provide electronic signals to an external imaging system in order to produce a two or three-dimensional image of the lumen, the arterial tissue, and tissue surrounding the artery. These images are generated in substantially real time and have a high degree of resolution. As an improvement over X-ray imaging, the transducers facilitate the construction of images of the exact site where the transducers are placed within the vessel.

Several ICUS/IVUS devices are now commercially available for sale in the United States and other countries. These devices include a transducer probe assembly having either a solid state transducer array or a rotating crystal. The physician is most interested in identifying the size and shape of the lumen, and any flaps or tears in the plaque, and these commercially available imaging devices facilitate the creation of detailed images of these relatively static features due to the relatively high frequency of ultrasound that they employ. Image signals are typically transmitted at frequencies between 10 and 40 MHz.

However, there is a common problem associated with these devices operating at such high frequencies. As the frequency of the ultrasound is raised, the backscatter from blood increases as the fourth power of the frequency. At frequencies of around 30 MHz, the amplitude of the backscatter from blood approaches the amplitude of the backscatter and reflections from the arterial tissue. Because of this phenomenon, the image of the lumen is filled with blood echoes, and it is often difficult to delineate the blood from the surrounding tissue. Therefore, this becomes confusing to the physician who is interested in defining the lumen.

A common method of detecting blood flow in ultrasonic systems used outside of the body is the use of a "Doppler" technique. The Doppler technique involves the detection of a change in frequency of a wave due to the reflection of the wave from a moving target. This technique is well established in radar literature such as M. Skolnik: "Introduction to Radar Systems", Second Edition, 1980. The Doppler technique, and variations of it, have been successfully applied to ultrasonic scanners used outside the body to provide color overlay maps of flow on top of grey scale images. A number of commercial systems utilizing this Doppler imaging technique are available, and are well known to those familiar with the state of the art.

However, the Doppler technique has its limitations when applied to arterial imaging. The Doppler technique relies upon the existence of a component of flow toward or away from the direction of the ultrasonic beam emitted by the transducer. In the case of cross-sectional arterial imaging, there is little or no component of flow to which the Doppler effect can be applied since substantially all flow is in a direction orthogonal to the ultrasonic beam.

A technique is known which attempts to extract a flow image from pixel data for a sequence of whole frame video images containing both flow and static portions. In this technique, pixel data for several whole frame video images are obtained over a period of seconds. In order to gather the data for each of the whole frame video images, an ultrasound transducer assembly transmits and receives a series of signals from all radial regions of the imaged volume in the vicinity of the transducer assembly. It is important to note that in gathering the data for the pixel data for a single whole frame video image, no two transduced echo signals in the set of received echo signals used to create the single whole frame video image are received from the same radial region of the imaged volume.

In this imaging technique, the process of gathering data for a single whole frame video image is repeated several times over a period of time of more than one second in order to obtain pixel data for a series of whole frame video images from which a single combined video image is to be created. Thereafter, the differences between values for corresponding pixel points within successive whole frame video images are averaged in an attempt to create a single frame image based upon the pixel data from the series of whole frame images. By averaging the differences between corresponding pixel data between frames, the resulting image is characterized by attenuation of features of the image that remain motionless for the entire frame gathering procedure which lasts on the order of more than one second. This is entirely unacceptable when one attempts to image the relatively dynamic vessels near the heart.

The above described technique, involving the comparison of the data from sequentially created whole frame images, represents an attempt to provide an image of dynamic features in a field of view containing both static and dynamic features. However, this imaging technique contains certain inherent limitations which reduce the utility of this imaging technique when applied to living vascular imaging in organisms. First, it takes more than a second (or even several seconds) to obtain a sufficient number of whole frame images to carry out the comparison and averaging of corresponding pixel values. Second, in a pulsatile artery, the vessel wall and moving intimal flaps are not motionless over a period of a second and therefore will not cancel out when the pixel values for corresponding positions in the whole frame images are compared. Third, cross-sections of a vessel in which blood flow stagnates provide a relatively static signal and therefore may be canceled out along with the rest of the other static portions of the image.

Additionally, it should be noted that the coronary tree, which comprises the vessels of primary interest to cardiologists, is the most rapidly moving vessel structure within the human body. When ultrasonic images of coronary arteries are made, the position of the tissue constantly changes during the data acquisition period due to the influence of the heart cycle upon the imaged tissue. Consequently, the image created by the dynamic vascular tissue will blend with the blood flow image if the above whole frame comparison technique is employed.

Furthermore, the relatively long data acquisition time required for the prior known technique prevents visual reproduction of the potentially useful dynamic information present in pulsatile flow.

SUMMARY OF THE INVENTION

It is a general object of the present invention to construct images of blood vessels wherein regions of blood flow are readily discernable from the vessel wall and surrounding tissue.

It is another object of the present invention to provide an apparatus that enables a viewer of an ICUS/IVUS image to easily differentiate between an image of the blood flow region in a vessel cross-section and a simultaneously displayed image of the vessel and surrounding tissue.

It is a related object of the present invention to display on a video monitor the blood flow region in a blood vessel in a manner which highly contrasts the blood flow region from the vessel wall and surrounding tissue.

It is another object of the present invention to construct the aforementioned images in a manner that visually appears to approach real-time imaging.

It is yet another object of the present invention to provide an adjustable image contrast for the user to find a maximum contrast between the blood flow region and the tissue under various circumstances.

The above and other objects are fulfilled in an apparatus and method for providing an image wherein the static features of an imaged region are substantially attenuated by combining a set of echo waveforms for a region of a cross-section obtained within a time period less than the minimum time period over which one can reliably depend on a vessel and surrounding tissue to remain substantially motionless.

In a flow imaging mode of operation, an ultrasound transducer assembly emits an ultrasound waveform from within a lumen of a vasculature. The ultrasound waveform propagates through a region within the vasculature. The emitted ultrasound waveform is reflected by blood and tissue in the region. The reflected ultrasound waveform is sensed by the transducer assembly and converted into an echo waveform. The above described emitting, sensing and converting functions are repeated a plurality of times for the region to obtain a set of echo waveforms for the region.

The resulting set of echo waveforms are combined to form a modified echo waveform representative of rate of movement of the blood and tissue in the region. Portions of the modified echo waveform representing dynamic regions contain large values while portions of the modified echo waveform representing static regions contain small values. Flowing blood is relatively dynamic, and therefore the portion of the modified echo waveform associated with flowing blood in the region comprises relatively large values. On the other hand, tissue is relatively static, and therefore the portion of the modified echo waveform associated with tissue includes relatively small values. The modified echo waveform is thereafter converted into a first image of the region. The first image prominently displays areas within the region containing flowing blood.

In order to better delineate the regions of flowing blood in a blood vessel, a second image of the region is generated prominently displaying the relatively static tissue within the region. Thereafter, the first image is combined with the second image for simultaneous display on a video display. In order to enhance the readability of the combined image, the portions of the combined image attributable to the first image are displayed in a distinct manner from the second image. In an embodiment of the present invention, the regions of flowing blood are colorized while the remaining portion of the combined image, including the tissue and other static features associated with the second image, are displayed in black and white.

In a further aspect of the invention, the blood flow image is colorized in order to enhance the contrast of the blood flow image when the images are combined to create a composite image with the second image. The resulting composite image is displayed on a video monitor.

Other objects and advantages not explicitly mentioned above will become apparent from the following detailed description of the drawings.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

FIG. 5d is an illustrative waveform demonstrating the result of subtracting the waveform illustrated in FIG. 5b from the waveform illustrated in 5a;

FIG. 8b is the frequency domain equivalent for the square wave modulation sequence illustrated in FIG. 8a;

FIG. 9b is the frequency domain equivalent for the time series modulation sequence illustrated in FIG. 9a;

FIG. 16b is the frequency domain equivalent for the four time series filter waveforms illustrated in FIG. 16a;

DETAILED DESCRIPTION OF THE PREFERRED EMBODIMENTS

A. Hardware Overview

Figure 1:
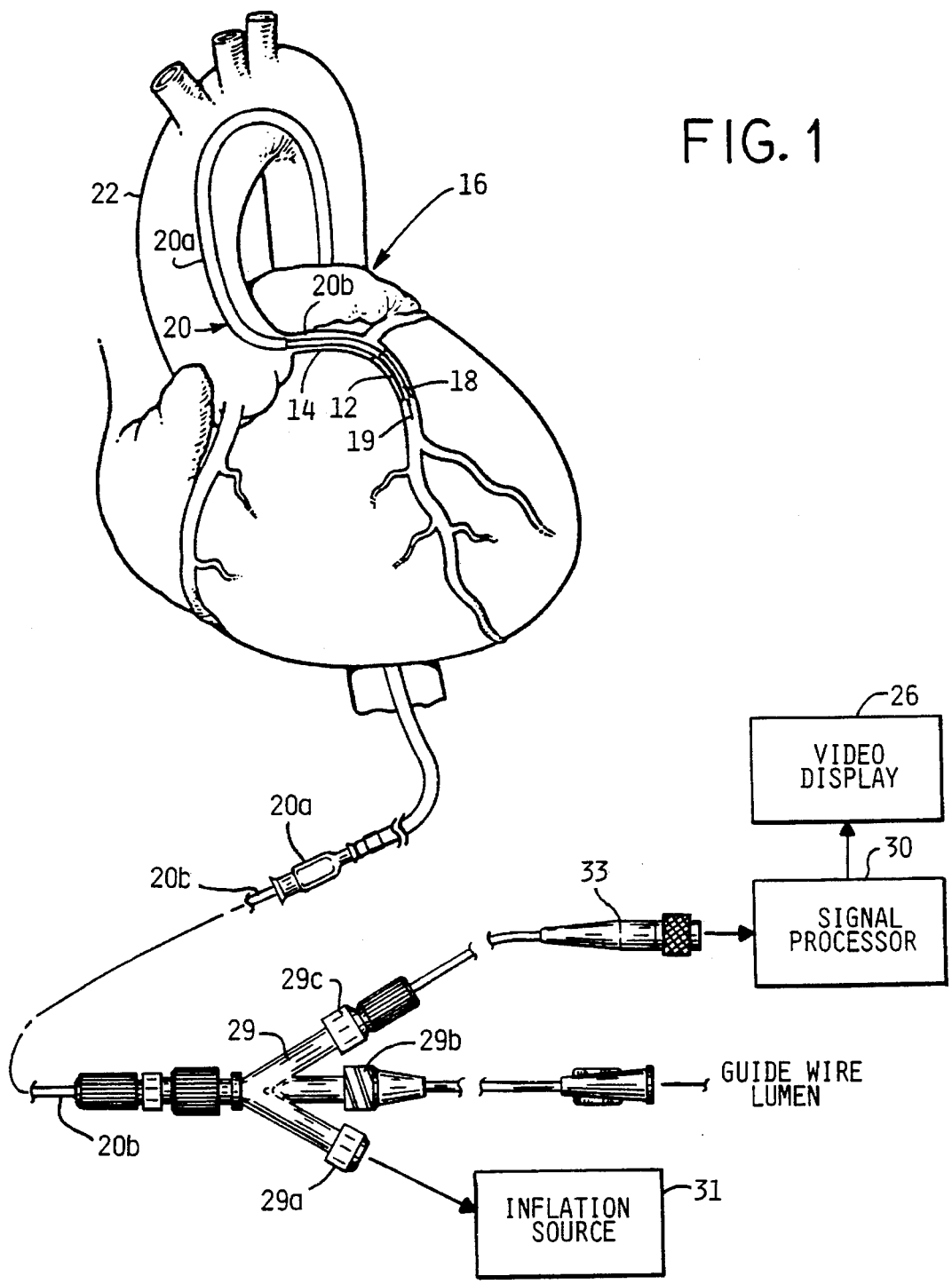
FIG. 1 is a schematic drawing of the ultrasound imaging system of the present invention and demonstrating the use of the device to image a coronary artery.
Figure 2:
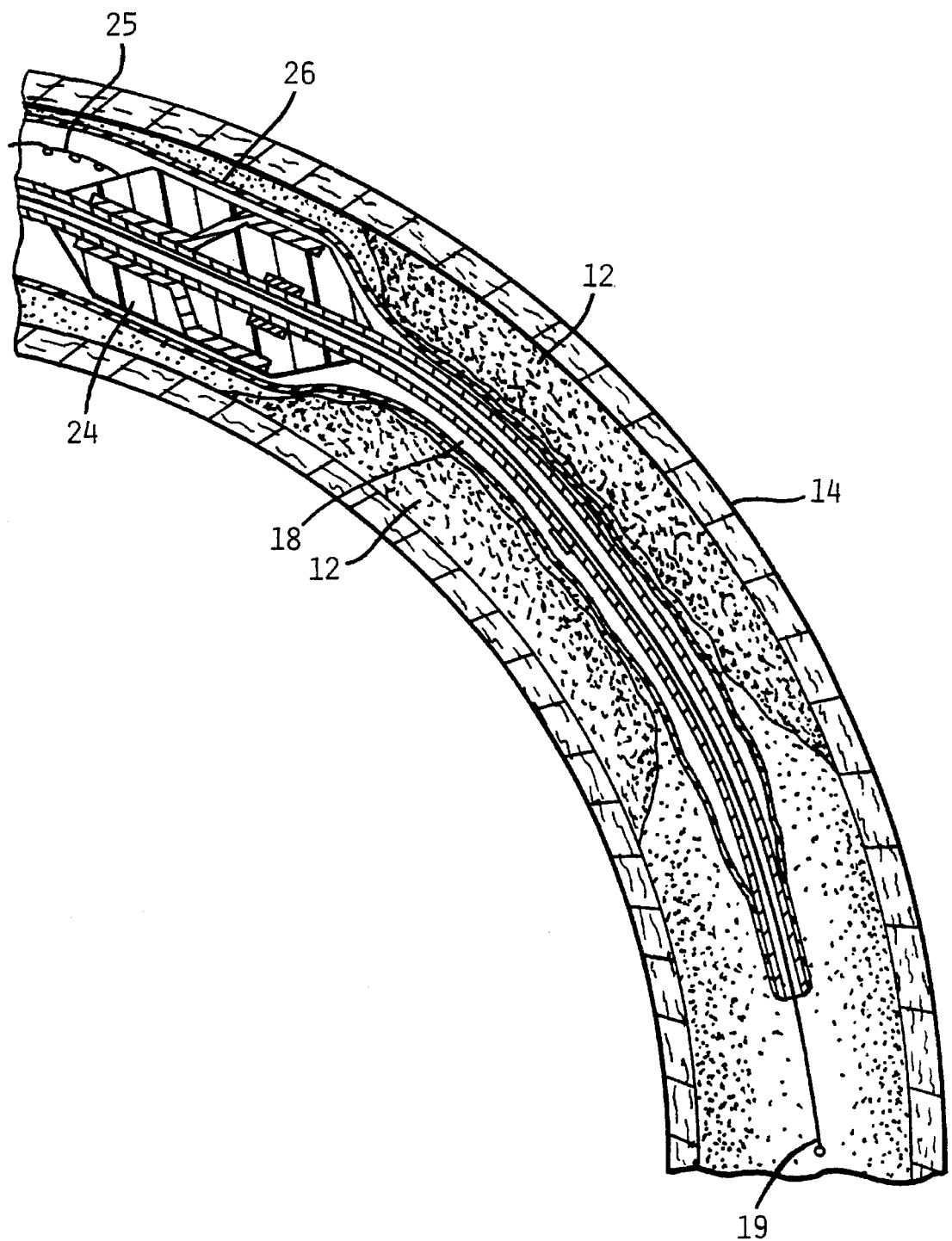
FIG. 2 is an enlarged and partially sectioned view of a portion of the coronary artery in FIG. 1 showing the probe assembly of the ultrasonic imaging device of the invention located in the catheter proximal to the balloon.

Turning to the illustrated embodiment and referring to FIGS. 1–2, a buildup of fatty material or plaque 12 in a coronary artery 14 of a heart 16 may be treated in certain situations by inserting a balloon 18, in a deflated state, into the artery via a catheter assembly 20. As illustrated in FIG. 1, the catheter assembly 20 is a three-part assembly, having a guide wire 19, a guide catheter 20a for threading through the large arteries such as the aorta 22 and a smaller diameter catheter 20b that fits inside the guide catheter 20a. After a surgeon directs the guide catheter 20a and the guide wire 19 through a large artery leading to the aorta 22, the smaller catheter 20b is inserted. At the beginning of the coronary artery 14 that is partially blocked by the plaque 12, the guide wire 19 is first extended into the artery, followed by catheter 20b, which includes the balloon 18 at its tip.

Once the balloon 18 has entered the coronary artery 14, as in FIG. 2, an ultrasonic imaging device including a probe assembly 24 housed within the proximal sleeve 26 of the balloon 18 provides a surgeon with a cross-sectional view of the artery on a video display 28. The probe assembly 24 comprises separate carrier and backing materials as disclosed in Eberle et al. presently pending U.S. patent application Ser. No. 08/012,251, filed on Feb. 1, 1993, and now U.S. Pat. No. 5,368,037 which is expressly incorporated herein by reference. The probe assembly 24 comprises an array of transducers fabricated from highly sensitive transducer materials of the type previously disclosed in the Eberle et al. '251 application. In the illustrated embodiment of the invention, the transducers emit 20 MHz ultrasound excitation waveforms. However, other suitable excitation waveform frequencies would be known to those skilled in the art. The transducers of the probe assembly 24 receive the reflected ultrasonic waveforms and convert the ultrasound echoes into echo waveforms. The amplified echo waveforms from the probe assembly 24, indicative of reflected ultrasonic waves, are transferred along a microcable 25 to a signal processor 30 located outside the patient. The catheter 20b ends in a threepart junction 29 of conventional construction that couples the catheter to an inflation source 31, a guide wire lumen and the signal processor 30. The inflation and guide wire ports 29a and 29b, respectively, are of conventional PTCA catheter construction. The third port 29c provides a path for the cable 25 to connect with the signal processor 30 and video display 28 via an electronic connector 33.

It should be noted that the present invention can be incorporated into a wide variety of ultrasound imaging catheter assemblies. For example, the present invention may be incorporated in a probe assembly mounted upon a diagnostic catheter that does not include a balloon. In addition, the probe assembly may also be mounted in the manner taught in Proudian et al. U.S. Pat. No. 4,917,097 and Eberle et al. U.S. Pat. No. 5,167,233, the teachings of which are explicitly incorporated, in all respects, herein by reference. These are only examples of various mounting configurations. Other configurations would be known to those skilled in the area of catheter design.

B. Description of the Signal Processor Hardware

Figure 3A:
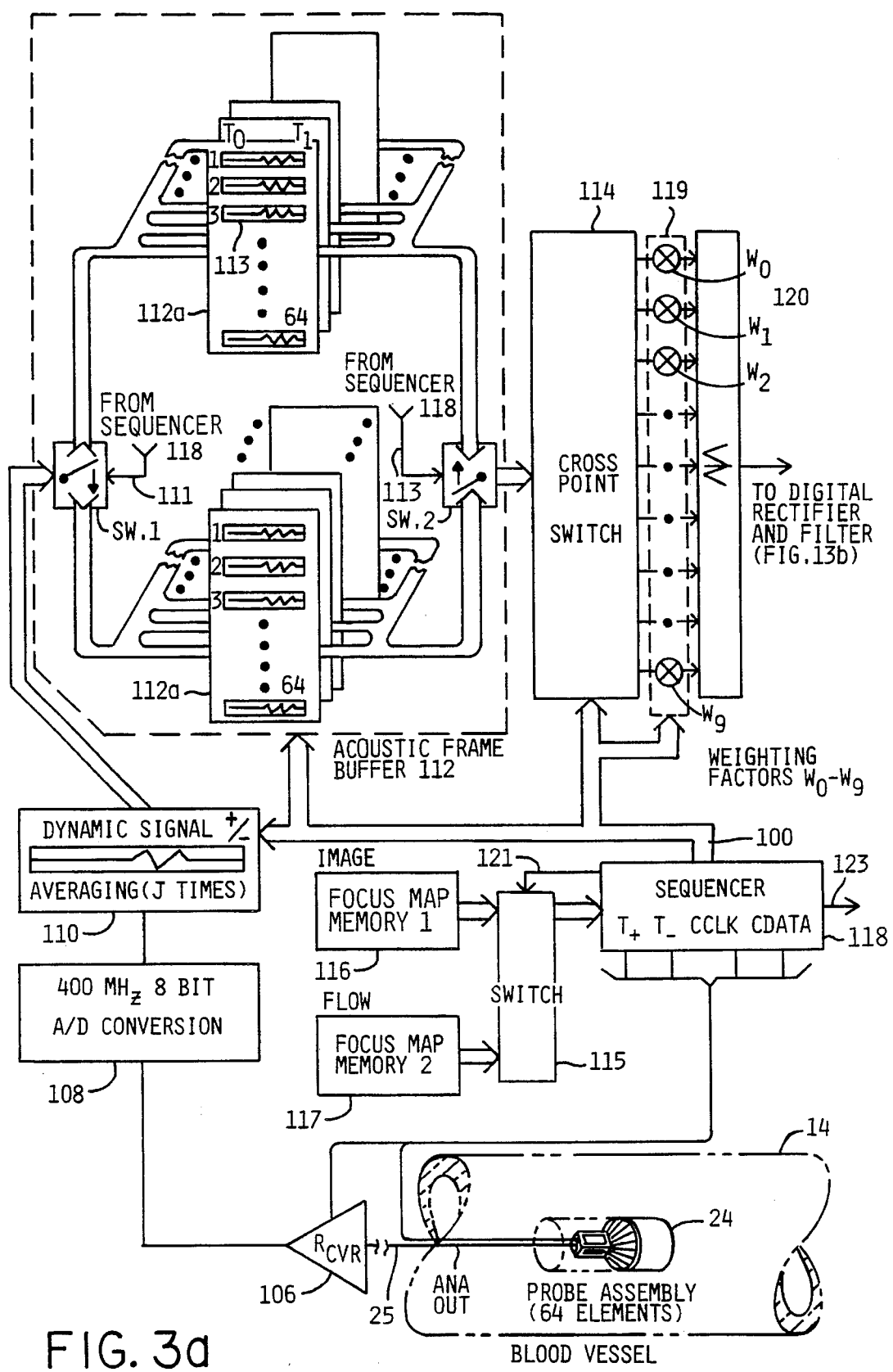
FIGS. 3a and 3b are schematic block diagrams of the signal processor and video display portion of the processing and imaging unit of the ultrasonic imaging device.
Figure 3B:
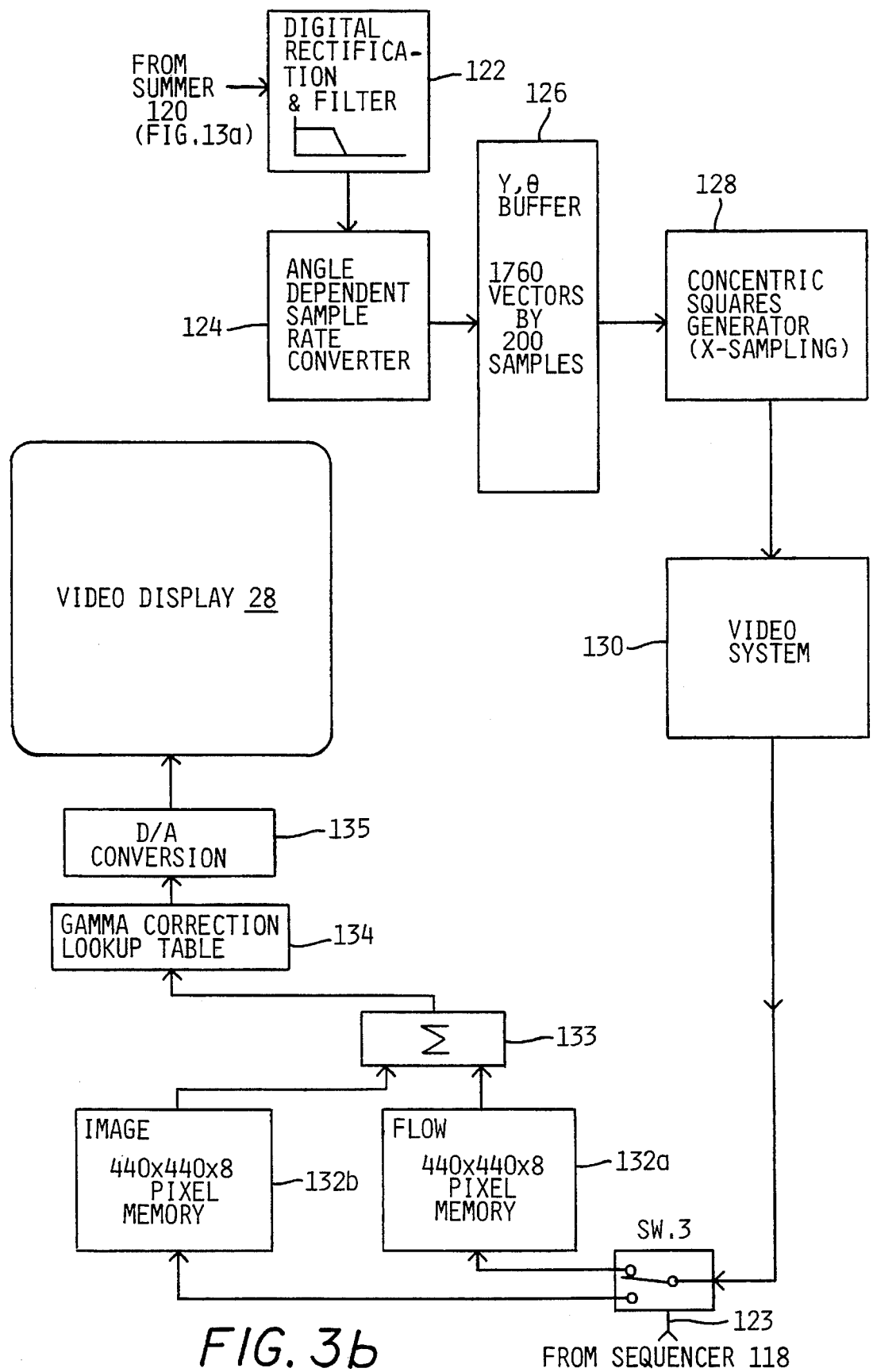

FIGS. 3a and 3b provide a schematic block diagram of the signal processor 30 and video display 28 of the ultrasonic imaging device. The ultrasound imaging system for carrying out the present invention is similar to the system described in the Proudian et al. U.S. Pat. No. 4,917,097 incorporated herein by reference. However, modifications were made to the system described in the Proudian et al. '097 patent, which will be apparent from the drawings and written description, to facilitate the implementation of a new method for creating an image from within a blood vessel. The image resulting from this new apparatus and method comprises an image arising from relatively static features in the field of view of the imaging apparatus and an image arising from relatively dynamic flowing blood.

Continuing with the description of FIG. 3a, the receiver 106 amplifies and transmits signals received from the probe assembly 24 to an analog to digital (A/D) converter 108. The A/D converter 108 converts analog signals from the receiver into 8-bit two's complement values at a frequency of 400 MHz. Higher or lower conversion rates may of course be utilized. However, a conversion rate of 400 MHz provides a sufficiently accurate digital record of the analog signals transmitted from the receivers 106 for purposes of carrying out the present invention.

In the illustrated embodiment of the invention, in combining the set of echo waveforms, the imaging system first converts the analog echo waveform into a set of digitized points referred to herein sometimes as a signal sample. The echo waveforms arise from echoes received by one or more transducer array elements after an excitation signal is emitted from one or more activated transducer array elements mounted upon the probe assembly 24. Each set of 2048 digitized points of a signal sample represents echo signals from targets within the tissue/blood medium which are received by the transducer over a time period starting from the transmit time and ending at a pre-determined time thereafter. The time at which an echo arrives is directly related to the distance of the target from the transducer by the velocity of ultrasound in the medium. The velocity is typically on the order of 1500m/s. The longer the time between the transmit signal and the received echo signal, the greater the distance the target is from the transducer.

In the illustrated embodiment of the invention, each signal sample comprises a set of 2048 digitized points, and each point is represented by a digital value having eight bits of resolution. The example of 2048 points collected at 400 MHz represents a time period of 5 μs, or 4 mm depth (note that a reflected ultrasound beam must travel to the target and back to the transducer). Of course each signal sample may comprise a number of points greater or less than 2048 points, and each point may be represented by a digital value having a greater or lesser number of bits of resolution.

Each digitized signal sample is transmitted from the A/D converter 108 to a dynamic signal averager (DSA) 110. Though not specifically shown in the drawings, the DSA 110 comprises a set of 8 ALU's for simultaneously processing a demultiplexed stream of digitized signals from the A/D converter 108. The functions executed by the DSA 110 differ from those of the DSA described in the Proudian et al. '097 patent. The DSA 110 of the present invention not only adds a set of digitized points of a signal sample to a previously accumulated set of point values arising from previously added signal samples, the DSA 110 is also capable of subtracting a set of digitized points of a signal sample from a previously accumulated set of point values stored in an accumulator register of the DSA 110. The carrying out of the described adding and subtracting functions in actual hardware would be known to those skilled in the area of computer arithmetic unit design.

A sequencer 118 transmits signals on the control bus 100 for governing the arithmetic and logical operation of the hardware elements schematically illustrated in FIGS. 3a and 3b. The sequencer 118 acts as the image processing control unit for the image processor schematically illustrated in FIGS. 3a and 3b. The arithmetic mode of the DSA 110 is determined by control signals transmitted on the control bus 100 by the sequencer 118. In the addition mode, the DSA 110 receives a set of digitized points of a signal sample from the A/D converter 108 and adds the set of digitized points of the signal sample to a previously accumulated set of point values in the accumulator of the DSA 110. In the subtraction mode, the DSA 110 receives a set of digitized points of a signal sample from the A/D converter 108 and subtracts the set of digitized points of the signal sample from a previously accumulated set of point values in the accumulator of the DSA 110 using two's complement subtraction. After J digitized signal samples have been processed by the DSA 110 (in a manner described hereinbelow), the accumulated point values for each of the 2048 sample points stored in the accumulator of the DSA 110 are transferred to an acoustic frame buffer 112. In the illustrated embodiment of the present invention, J equals 256.

The acoustic frame buffer 112 is unchanged from the frame buffer previously described in Proudian et al. U.S. Pat. No. 4,917,097, which has been incorporated by reference. In order to accommodate loading of a first portion of the acoustic frame buffer 112 while reading from a second portion, the acoustic frame buffer 112 is bifurcated. Data loaded into the acoustic frame buffer 112 is selectively routed through a switch 1 to either of the two sections in accordance with control signals transmitted by the sequencer 118 on line 111. Furthermore, as previously explained in the Proudian et al. '097 patent, the acoustic frame buffer 112 includes a plurality of memories 112a, each memory 112a having a full set of imaging data. In the illustrated embodiment of the invention, there are ten (10) memories 112a for each of the two sections, in order to facilitate parallel reading of ten (10) data values into the inputs of a crosspoint switch 114.

Data stored in the acoustic frame buffer 112 is selectively routed from either section of the acoustic frame buffer 112, through switch 2 (in accordance with control signals transmitted by the sequencer 118 on line 113), and to the cross point switch 114. An image focus map memory 116 provides control signals to the sequencer 118 which in turn uses the control signals to control the retrieval of data from the acoustic frame buffer 112 and the operation of the cross point switch 114 and multiplier 119 in a manner previously described in Proudian et al. U.S. Pat. No. 4,917,097 in order to calculate an image value for each focus point in an image constructed from the ultrasound signal samples stored in the acoustic frame buffer 112.

In addition to the image focus map memory 116, the ultrasound imaging system incorporating the present invention includes a flow focus map memory 117. The flow focus map memory 117 operates in substantially the same manner as the image focus map memory 116 to provide control signals to the sequencer 118 which in turn uses the signals to control the retrieval of data from the acoustic frame buffer 112, the passing of the data through the cross point switch 114, and the modification of the data by the multiplier 119 in accordance with a flow image construction method described hereinbelow.

In general, the differences between the contents of the image focus map memory 116 and the contents of the flow focus map memory 117 reflect the differences in the excitation signals used to create the signal samples from which images are constructed and the method utilized by the signal processor to construct an image from the signal samples. The delay values provided by the flow focus map memory 117 for a given point are of a similar form to those provided by the imaging focus map memory 116, except that since there is no reconstruction of the flow data, there is no delay or summation between neighboring sets of data, and the data passes through the cross-point switch 114 with a unity value applied to one of the weighting factors of the multiplier 119, for example $W_0$, and zeros are applied to the remaining weighting factors $W_1$–$W_9$; the control signals provided by the flow focus map memory 117 to the cross point switch 114 and the multiplier 119 are altered in a manner which will be apparent to those of ordinary skill in the area of ultrasound image construction in view of the flow image construction method described herein below.

A switch 115 selectively routes the signals from either the image focus map memory 116 or the flow focus map memory 117 in accordance with a signal provided on line 121 from the sequencer 118. It will be appreciated by those skilled in the art that even though focus control data is provided by two separate memory modules 116 and 117, the two separate focus map memories can be combined into a single memory module.

The sequencer 118 distributes control signals to the various components of the ultrasound imaging system in a manner similar to the one previously described in Proudian et al. U.S. Pat. No. 4,917,097 (incorporated by reference). The control signals from the sequencer 118 synchronize data reception, digitization, storage and analysis. The sequencer disclosed in the Proudian et al. '097 patent has been modified to provide the control signal on line 121 to the switch 115 to select either one of the focus map memories 116 and 117. Furthermore, the sequence 118 provides a signal on the control bus 100 to select the mode of operation of the DSA 110.

After weighting values are applied to signals from the cross point switch 114 by the multiplier 119, the signals are transmitted to a Wallace adder 120. The Wallace adder 120 combines the results from the multiplier 119 in order to obtain image data signal values corresponding to focus points on focus beams within an image.

Turning to FIG. 3b, signal values from the Wallace adder 120 are transmitted to a digital rectifier/filter 122 wherein the signal is rectified and then processed by a low-pass filter in a known manner. At this point the image data comprises focus point values for various locations expressed in polar coordinates. Before storing the image data in video memory and displaying the image data on a video screen, the locations of the focus points are mapped from polar coordinates to pixel positions in the display space of the video display 28.

In order to facilitate the storage of the image data in video memory, the rectified and filtered signals are passed to an angle-dependent sample rate converter 124. The sample rate converter 124 maps each of the focus point values calculated by means of the previously described signal processing hardware to a vertical position corresponding to a nearest horizontal grid line for the video display 28. After assigning vertical positions to the focus point image data, the resulting image data is transferred to a Y/Θ memory buffer 126.

The image data stored in the Y/Θ memory buffer 126 is passed to a concentric squares generator 128 wherein each of the focus point values is mapped to a horizontal position corresponding to a nearest vertical grid line for the video display 28. At this point, the focus point image data from the digital rectifier/filter 122 has been completely mapped to nearest pixel points on a video display 28.

The resulting pixel values are transmitted to a video system 130 which selectively places the data into either a flow pixel memory 132a or an image pixel memory 132b based upon the state of the switch 3. The state of the switch 3 is controlled by a signal transmitted by the sequencer 118 on line 123.

In order to achieve contrast between a flow image stored in the flow pixel memory 132a and a static image stored in the image pixel memory 132b, a chromatic bit is set in the flow pixel memory 132a at each pixel position of the flow image evidencing a region of blood flow. If the magnitude of a signal in the flow image corresponding to a pixel is zero, or less than a threshold value adjusted by means of control values submitted by the operator, then the chromatic bit is not set and the corresponding pixel in the flow pixel memory 132a is not colorized.

Though contrast is enhanced between the flow regions in the flow image and the static image by colorizing the flow regions in the flow image stored in the flow pixel memory 132a, contrast between the flow image and the static image may alternatively be achieved by colorizing the features captured in the static image rather than the flow image. In that case, the chromatic bit is cleared in each pixel position of the displayed image wherein the signal in the flow image corresponding to the pixel position does not exceed the threshold. Other modes of applying contrasting display characteristics to the combined static and flow images to enable a user to readily distinguish between static and dynamic features in order to quickly identify the flow regions of a blood vessel would be known to those skilled in the art in view of the above description.

After the pixel image data for the non-flow and flow images has been stored in the image pixel memory 132b and flow pixel memory 132a, respectively, a summing circuit 133 sums each pixel point value in the flow pixel memory 132a with a corresponding pixel point value in the image pixel memory 132b. The summed video signal is transmitted by the summing circuit 133 to a gamma correction lookup table 134.

The gamma correction lookup table 134 performs well known modifications to the video image data transmitted from the summing circuit 133. Thereafter, the digital video data is transmitted to a digital-to-analog converter 135 which converts the digital pixel data into analog data for controlling the video display 28.

Having described the signal processing system hardware of the present invention, a process is now described for simultaneously displaying an image of a vessel showing both flow and tissue data.

Figure 4:
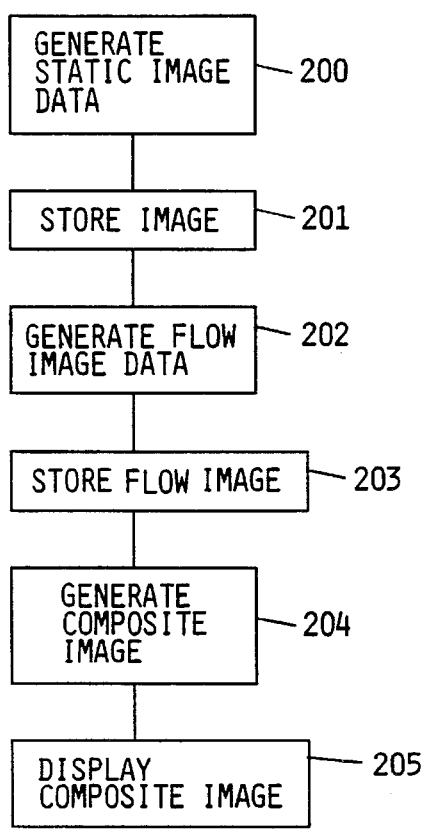
FIG. 4 is a flow chart summarizing the steps for creating a composite flow/static image of a vessel.

Turning now to FIG. 4, a flow chart is provided summarizing the steps for creating a composite flow/tissue image of a blood vessel. At step 200, the ultrasound imaging system operates in a mode for acquiring image data showing primarily the static features of an imaged region previously described in the Proudian et al. U.S. Pat. No. 4,917,097 (incorporated herein by reference).

C. Description of the Static Imaging Mode

The following is a brief summary of the steps previously described in the Proudian et al. U.S. Pat. No. 4,917,097 for producing an image based upon the summation of signals arising from echo signals produced by J excitation signals from a single transducer in a very short time period. In the imaging mode a transducer on the probe assembly 24 is activated by the sequencer 118. Next, the sequencer 118 sends a transmit signal to the probe assembly 24, and the activated transducer emits ultrasonic energy into the vessel. Ultrasonic echoes return to a transducer assembly from both the blood and the tissue.

When the transducer assembly is in direct contact with the blood, the echo signals from the blood are typically the first to be received by the transducers. The stronger echo signals from the relatively stationary vessel walls are received by the transducers after the blood echo signals. The ultrasonic echoes from both the vessel walls and the blood are converted into electrical signals by the transducers and buffered by transimpedance amplifiers within the integrated circuits on the probe assembly 24. The buffered electrical signals are transmitted via the microcable 25 to the receiver 106. The electrical signals transmitted from the probe assembly 24 via the microcable 25 are further amplified and filtered by the receiver 106 before being transmitted to the A/D converter 108.

Figure 5A:
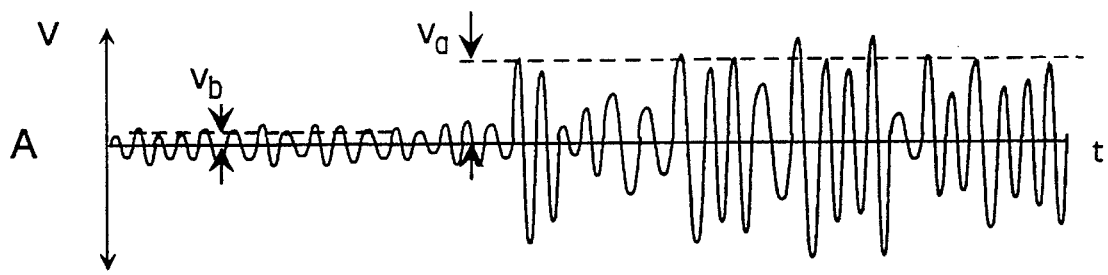
FIGS. 5a and 5b are representative waveforms of transduced echo waveforms in analog form resulting from consecutive excitation signals from a transducer spaced very close in time.
Figure 5B:
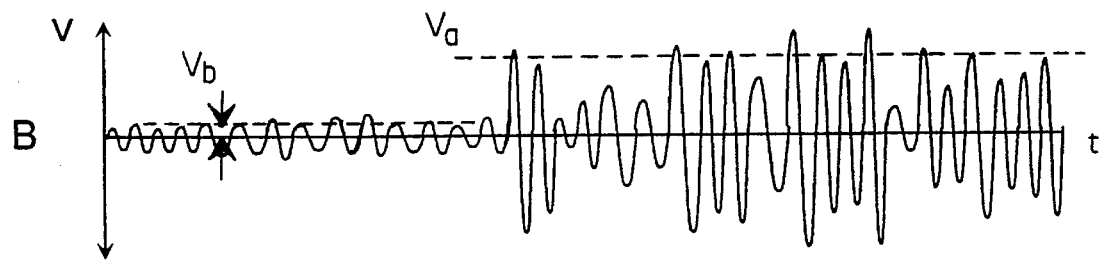

FIGS. 5a and 5b are illustrative representations of transduced echo signals graphically illustrated in the analog form resulting from consecutive excitation signals spaced very closed in time emitted from a transducer assembly. Whereas FIGS. 5a, 5b, 5c and 5d are used to illustrate the principles of the present invention in analog form, it should be noted that the methods of the present invention are preferably performed in the digital form in order to simplify the necessary hardware using modern methods of electronic engineering. The principles illustrated in FIGS. 5a, 5b, 5c and 5d apply equally to the digital form provided that the sampling rate of the analog waveform for the transduced echoes at the A/D Converter 108 is sufficiently high to preserve the phase of the analog signal. This is achieved through high sampling rates (e.g., 16 to 20 times the maximum frequency of the ultrasound), or through sampling and interpolation techniques wherein the sampling rate is reduced, but the sample points are digitally interpolated to restore more accurate phase information using suitable filters. The latter sampling technique of Saugeon U.S. Pat. No. 4,787,392 is incorporated herein by reference.

As is known in the art, the creation of signal samples from received echo signals arising from each of the J excitation signals are synchronized such that echoes from a same distance from the surface of a receiving transducer are located in the same relative location of the signal sample. In the illustrated embodiment of the present invention, each digitized signal sample comprises a set of 2048 points. As a consequence of synchronized reception of the echo signals for the creation of digitized signal samples, each same numbered one of the set of 2048 points for each of the digitized signal samples corresponds to substantially a same distance from the surface of a receiving transducer as a same numbered point in the other digitized signal samples (e.g., point 10 in each of the signal samples corresponds to a same distance from the receiving transducer surface as point 10 in each of the other sets of 2048 points comprising the J digitized signal samples).

Furthermore, portions of the received echo waveforms (which are received and converted into digitized signal samples) are sometimes identified herein as belonging to either a first, relatively dynamic, portion; or a second, relatively static portion. The values of corresponding digitized points associated with the first portion of the echo waveform change from signal sample to signal sample in the set of J signal samples. The values of corresponding digitized points associated with the second portion of the echo waveform remain substantially unchanged from signal sample to signal sample in the set of J signals samples. The significance of the difference in behavior between the first and second portions is explained below in conjunction with two distinct imaging modes of the ultrasound imaging catheter.

FIGS. 5a and 5b illustrate typical echo waveforms for transduced echo signals resulting from the weaker, random echo signals from the blood arriving first at the transducer and the stronger, unchanging echo signals from the tissue arriving after the blood echo signals. The first portion of the echo waveform for the transduced echo signals in FIGS. 5a and 5b, having a root-meansquare (RMS) magnitude of $V_b$ represents the relatively dynamic portion of the signal arising from transduced echo signals primarily from blood. The second portion of the waveform for the transduced echo signals in FIGS. 5a and 5b, having an RMS magnitude of $V_a$, represents the relatively static portion of the signal arising from transduced echo signals primarily from tissue. For purposes of this illustration, the RMS values are a measure of the average magnitude of the echo waveforms resulting from reflections of the emitted ultrasound waveform over a distance of interest within the blood or tissue, that is, sub-sets in time of the 2048 points in the digitized signal sample.

The A/D converter 108 transforms the analog signals from the receiver 106 into digital data at a rate of 400 MHz with 8 bits of amplitude resolution. The digitized information is then sent to the DSA 110. During the static imaging mode, the sequencer 118 transmits a control signal to the DSA 110 to cause the DSA 110 to operate continuously in an addition mode. In the addition mode, wherein a number of digitized signal samples are added together, the DSA 110 performs a repeated read-modify-write operation. The read-modify-write operation comprises summing together a new digitized signal sample comprising 2048 points with data previously stored in an accumulator corresponding to the 2048 points, then storing the resulting summed values for the 2048 points back in the accumulator register. In order to reduce the speed requirements of the electronic circuits which perform this function, the 2048 points are demultiplexed to 8 sets of 256 points each at 50 MHz. Each set is separately processed by a one of the eight (8) ALU's of the DSA 110.

While in the static imaging mode, the arithmetic logic units (ALUs) of the DSA 110 which perform the addition operations remain in the addition mode while a total of J digitized signal samples resulting from J repetitions of a same excitation and read pattern are summed by the DSA 110. In the illustrated embodiment, J equals 256. Therefore, a set of 256 digitized signal samples (each digitized signal sample comprising 2048 points) are summed by the DSA 110 to provide echo information for a region of the vasculature. The set of 256 digitized signal samples arise from a set of 256 transduced echo waveforms, which in turn, arise from 256 separate excitation signals emitted from an activated transducer and propagated into the blood vessel. The resulting summations of the corresponding 2048 points of the 256 digitized signal samples are stored in the acoustic frame buffer 112 without further processing. However, the resulting sum from the DSA 110 may be divided by the number of summed samples (or any other number) or bit shifted to provide an average value per sample or per a number of samples.

Figure 5C:
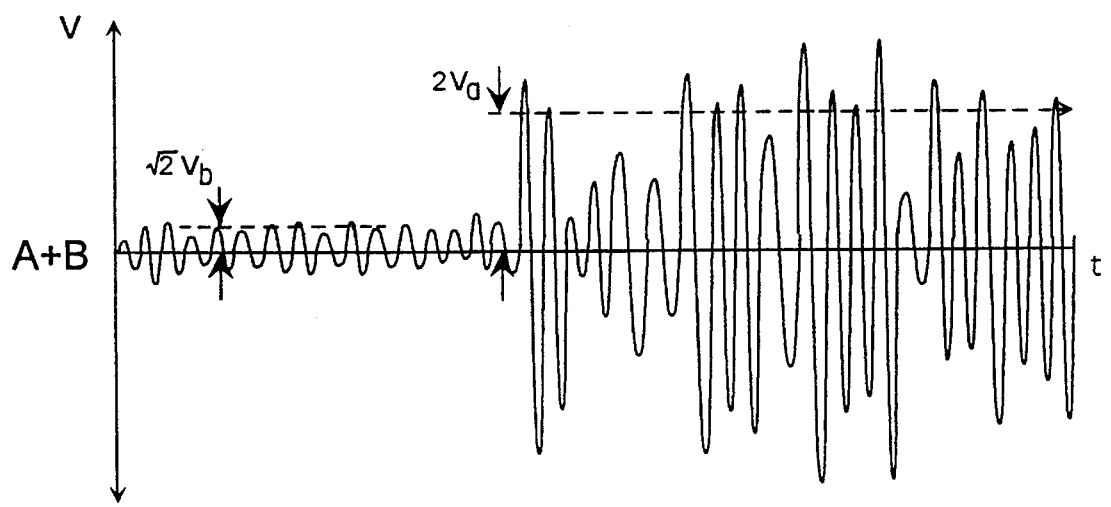
FIG. 5c is an illustrative waveform demonstrating the result of adding the waveform illustrated in FIG. 5a to the waveform illustrated in FIG. 5b.

The purpose of the above-described summing process is to improve overall signal quality and reduce the magnitude of signals arising from noise and dynamic features of an imaged region in relation to the signals arising from static features in the imaged region in order to create an image displaying the relatively stationary features of a blood vessel and surrounding tissue. The effect of the summing process for two exemplary consecutive signal samples A and B, is illustrated in FIG. 5c. The transduced signal samples from the tissue, having an RMS magnitude of $V_a$, are unchanged from signal sample to signal sample when the samples are created in a very short time span, and therefore the signal samples from the tissue sum coherently. Summing 256 transduced echo signal samples arising from the tissue and received by a transducer amplifies the RMS magnitude of the signal samples from the tissue by a factor of 256, or about 48dB. This analysis, of course, assumes that the tissue is absolutely static. In actuality, the echo signals from the tissue, though relatively static, are not absolutely static and the degree of amplification is a value less than 256. However, purely static tissue is a satisfactory assumption for purposes of describing the illustrated and alternative embodiments of the present invention.

On the other hand, the transduced signals for the blood, having an RMS magnitude labeled $V_b$, in FIG. 5a, which are relatively dynamic in comparison to the tissue signals, do not sum coherently, and the amplification of the RMS amplitude of the summation of the transduced signals from the blood, relative to the amplification of signal samples arising from stationary features, is reduced.

In a purely random media, the amplification achieved by summing together a number of signal samples is only equal to the square root of the number of summations. Therefore, a summation of 256 transduced echo signal samples from a purely random media amplifies the RMS value of the individual signals by a factor of the square root of 256, or 24dB.

In actuality, blood may contain both static and dynamic components. Summing 256 transduced echo signal samples arising from moving blood produces a summed signal having an amplification which is considerably less than 256 (due to the random components of the blood), but greater than the square root of 256 (due to the static components of the blood). Therefore, summing a large number of signal samples of the blood and tissue in a region obtained over a very short period of time reduces the relative magnitude of the summed echo signals caused by moving blood or noise (which are both relatively random in nature) in comparison to the magnitude of the summed echo signals from static features. However, stagnating blood will substantially contribute to the summed signal obtained from multiple signal samples of echo signals and should be accounted for when selecting a signal filtering scheme.

As previously explained above and in the Proudian et al. '097 patent, the DSA 110 transmits a set of 16 bit data for a selected one of the 64 total transducer elements (resulting from the summation of the 256 signal samples at each of the 2048 digitized signal sample points) to the acoustic frame buffer 112 for storage and subsequent image construction processing. The sequencer 118 then transmits control signals to the probe assembly 24 in a known manner to select a next transducer element in the array and repeats the previously described signal sample summation process J times for the next transducer element. The transduced signal sample collection and summation process described above is repeated until 64 summed sets of 16 bit data of the type described hereinabove (one set for each of the 64 transducer elements on the probe assembly 24) have been written into the acoustic frame buffer 112. Each of the summed sets contains a total of 2048 individual 16-bit summation values. Each one of the 2048 16-bit summation values corresponds to one of the digitization points for the sampled signals.

After the static image construction data has been gathered and stored in the acoustic frame buffer 112, the sequencer 118 selects the image focus map memory 116 via the control line 121 to the switch 115. The image focus map memory 116 provides all of the delays and weightings for the cross-point switch 114 and multipliers 119 for producing an image signal value for each focus point of a displayed ultrasound image. The results from the multiplier circuit 119 are transmitted to the Wallace adder 120. The summed value from the Wallace adder 120 for a focus point is then transmitted to the digital rectifier and filter 122 for processing in a manner described hereinabove in conjunction with the hardware description of the ultrasonic imaging system.

The angle dependent sample rate converter 124, Y/Θ buffer 126, and concentric squares generator 128 map the values for focus points, obtained from the digitized and summed transducer signals, from polar coordinates to the nearest corresponding pixel locations in a video display. The image data corresponding to the pixel locations is then transmitted to the video system 130.

Returning to FIG. 4 summarizing the steps of the imaging process, after the pixel values are calculated for the ultrasound image (at step 200), control then passes to step 201. At step 201, the resulting pixel values for the image acquired while the ultrasound imaging system operates in the imaging mode are selectively transmitted via the video system 130 through the switch 3 (controlled via line 123 from the sequencer 118). Thereafter, the pixel values are stored within the image pixel memory 132b. Thereafter, control passes to step 202 wherein the ultrasound imaging system of the present invention generates flow image data in a manner described herein below.

Before continuing with the description of step 202, it should be noted that after the image pixel data is loaded into the image pixel memory 132b at the conclusion of step 201, the imaging system immediately generates an image on the video display 28 based upon the present image data even though a flow image has not yet been produced (in accordance with steps 202 and 203). Furthermore, once the image pixel memory 132b and the flow pixel memory 132a have been loaded with data, the image displayed upon the video display 28 is revised each time a new set of image data is loaded into either the flow pixel memory 132a (after step 203) or the image pixel memory 132b (after step 201).

D. Description Of The Flow Imaging Mode

1. Overview Of The Flow Imaging Mode

Figure 6:
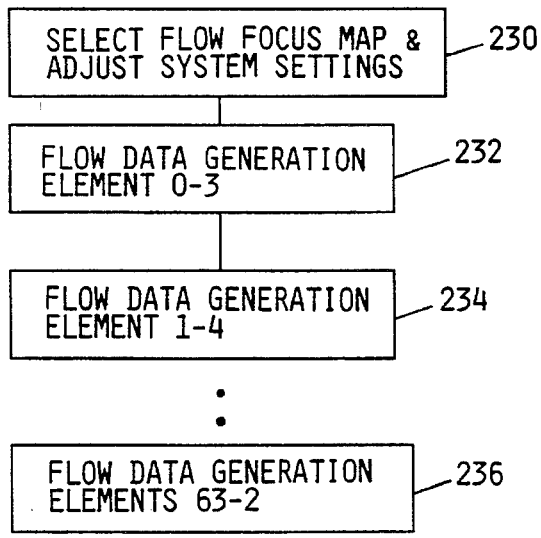
FIG. 6 is a flow chart summarizing the steps for acquiring flow image data for an ultrasound imaging system having a transducer array including 64 transducers which are activated for emitting an excitation signal in groups of 4 transducers.

The general steps of the flow image data acquisition process for an illustrated embodiment of an ultrasound imaging system are summarized in FIG. 6. While operating in the flow imaging mode and executing the steps summarized in FIG. 6, the ultrasound imaging system operates in a fundamentally distinct mode from the previously described static imaging mode. In contrast to the DSA 110 repeatedly executing addition operations on J digitized signal samples while the ultrasound imaging system operates in the static imaging mode, the DSA 110 operating in the flow imaging mode alternatingly adds and subtracts a set of J digitized signal samples in a balanced manner. As will be further explained herein below in conjunction with FIGS. 5a, 5b and 5d, this method of combining the signal samples results in significant attenuation of portions of the signal samples arising from the echoes produced by relatively stationary features such as tissue while the portions of the signal samples arising from the echoes produced by relatively non-stationary blood are amplified.

Figure 5D:
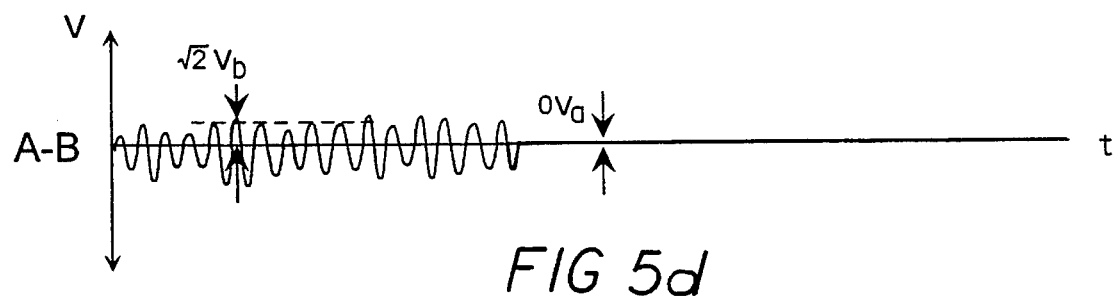

FIGS. 5a, 5b, and 5d illustratively depict the effect of balanced addition and subtraction of signals having a purely random portion and a static portion. The first portion of the signal samples A and B in FIGS. 5a and 5b respectively, having a constant RMS magnitude of $V_b$, is assumed to be random from signal sample to sample. The second portion of the signal samples A and B, having a constant RMS magnitude of Va, is assumed to be static (identical from sample to sample). FIG. 5d represents the signal resulting from subtracting signal sample B from signal sample A.

The first portion of the signal in FIG. 5d, illustrating the result of subtracting the random portion of signal sample B from the random portion of signal sample A, has a non-zero RMS magnitude equal to the square root of the number of combined samples times $V_b$. In FIG. 5d, the number of combined samples is two. This amplification is the same as the amplification obtained by adding all of the signal samples. On the other hand, the second portion of the signal in FIG. 5d illustrating the result of subtracting the static portion of signal sample B from the static (identical) portion of signal sample A has a constant zero magnitude.

Though the above example includes only two (2) signal samples, the effect of combining signal samples having a random and a static portion is applicable to the generalized case where a sequence of received signal samples are alternatingly added and subtracted in a balanced manner. The magnitude of the random portion of the alternatingly added and subtracted signal samples is amplified by a factor equal to the square root of the number of combined signal samples. For example, for 256 signal samples alternatingly added and subtracted in a balanced manner, the random portion of the signal samples will be amplified by a factor of up to the square root of 256, or 24dB. The magnitude of the static portion of the 256 alternatingly added and subtracted signal samples approaches zero.

In view of the above discussion concerning alternatingly adding and subtracting signal samples, alternatingly adding and subtracting signal samples arising from transduced ultrasound echoes in the DSA 110 substantially amplifies the random echo signals from moving blood and attenuates the relatively static (unchanging) echo signals from the tissue and non-moving blood. In actuality, the echo signals produced by moving blood are not purely random and the echo signals produced by tissue are not absolutely static, but such assumptions approximate the relative nature of the transduced echo signals and are appropriate for describing the present invention. The ultrasound flow imaging technique described below utilizes the signal amplification behavior of blood and tissue echoes to generate flow image data by alternatingly adding and subtracting, in a balanced manner, a series of signal samples obtained over a very short time period.

2. System Set-up and Adjustment

Turning now to FIG. 6 which summarizes the steps comprising the flow imaging mode, at step 230 the ultrasound imaging system selects the flow focus map memory 117 and adjusts system settings for carrying out flow imaging. The sequencer 118 transmits a control signal on line 121 to the switch 115 to connect the flow focus map memory 117 to the sequencer 118 thus enabling the flow focus map memory 117 to provide control signals to the cross-point switch 114, multiplier 119 and Wallace adder 120. The sequencer 118 also transmits control signals via the control bus 100 to the DSA 110 for controlling the arithmetic mode of the DSA 110 while sets of J digitized signal samples are received and processed by the signal processor 30.

The sequencer 118 (at step 230), in contrast to the static imaging mode (having one active emitting/receiving transducer element at any time), activates the channels associated with four adjacent transducers on the probe assembly 24. Because four transducers emit four times the energy emitted from a single transducer, the echo signal samples from the moving blood are substantially higher than background or thermal noise generated by the probe assembly 24. However, because the total ultrasonic energy emitted and received by the four transducers is much higher than the energy associated with a single activated transducer in the imaging mode, in order to avoid saturation, the sequencer 118 transmits a control signal to the receiver 106 reducing the gain of the receiver 106.

Figure 11:
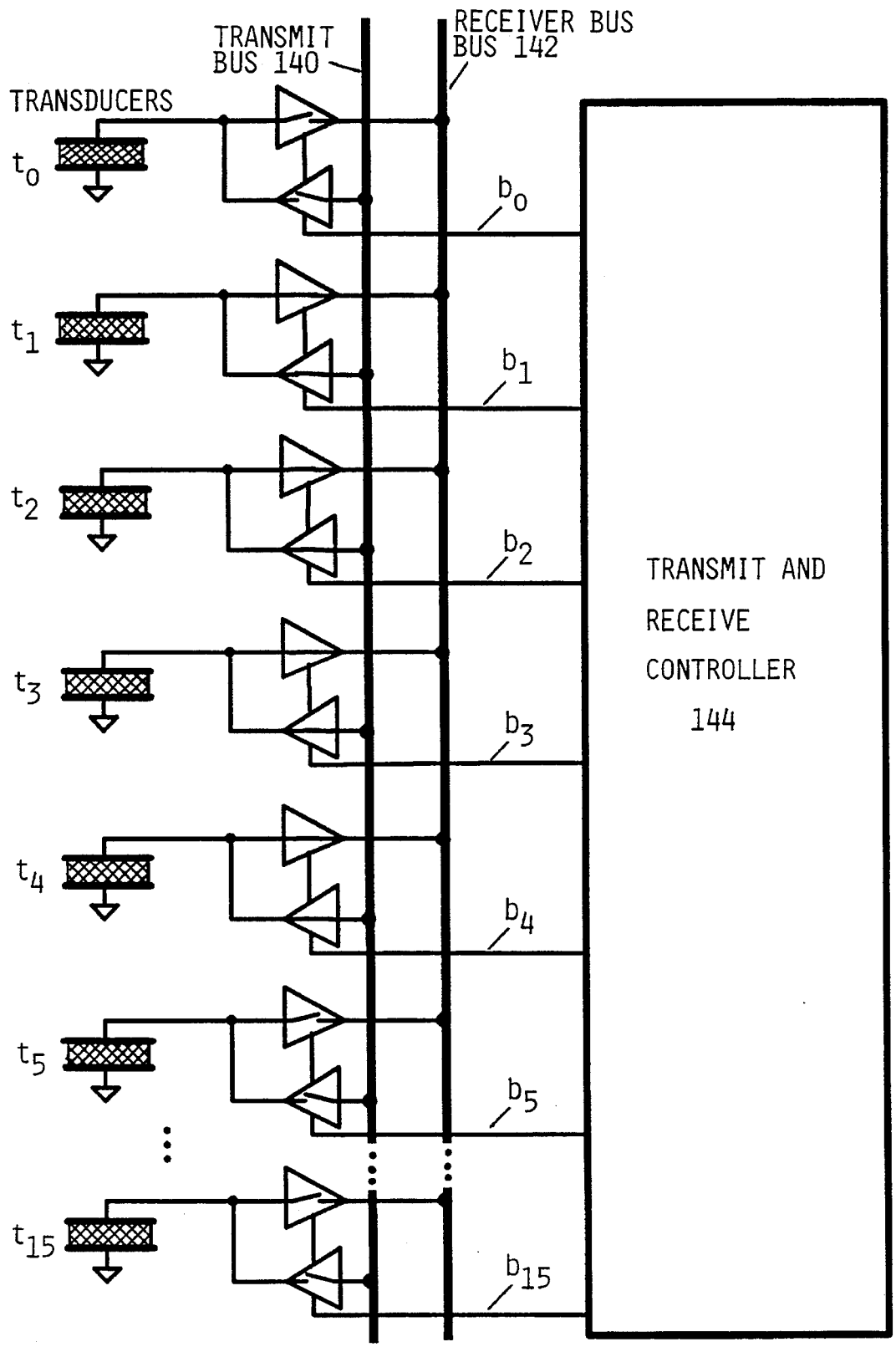
FIG. 11 is a schematic drawing showing an exemplary scheme for connecting a set of transducers of the probe assembly to a transmit bus and a receive bus.

Turning to FIG. 11, a schematic drawing is provided illustratively depicting the connection scheme of a set of transducers t of the probe assembly 24 to a transmit bus 140 and a receive bus 142 while the ultrasound imaging system operates in the flow imaging mode. A more detailed description of the electronic circuitry carried on the probe assembly 24 is provided by the Proudian et al. '097 patent which is incorporated herein by reference. Though only 16 transducers ($t_0$–$t_{15}$) are depicted in FIG. 11, the probe assembly 24 in the illustrated embodiment comprises a total of 64 transducers in accordance with the previous description of the electronic circuitry described in the Proudian et al. '097 patent which is incorporated by reference. The transmit bus 140 and receive bus 142 are coupled to all 64 transducers t to support simultaneous connection of sets of the transducers t to the transmit bus 140 and the receive bus 142.

In the illustrated embodiment of the electronic circuitry carried on the probe assembly 24 for generating and receiving ultrasound waveforms, described in the Proudian et al. '097 patent, a transmit and receive controller 144 comprises shift registers, each one of the bits of the shift registers being matched with one of the transducers t. Signals on buffer control lines $b_0-_{15}$ control the connection of the transducers $t_0-t_{15}$ to the transmit bus 140 and the receive bus 142 via transmit and receive buffers associated with the transducers t.

In accordance with the illustrated embodiment of the present invention, while operating in the flow imaging mode, the transmit and receive controllers transmit active control signals on four (4) buffer control lines b to simultaneously enable the transmit and receive buffers for four (4) adjacent transducers. For example, the schematic drawing in FIG. 11, transducers $t_1-t_4$ are selected, via buffer control lines $b_1-b_4$, for both emitting ultrasonic waveforms and receiving ultrasonic echoes from the imaged region in accordance with step 234 of FIG. 6. The transduced echoes from the four adjacent transducers ($t_1-t_4$) are passed through the buffers and the resulting electrical current signal from each buffer is combined and transmitted to the microcable 25 via the receive bus 142.

3. Raw Flow Image Data Acquisition

Continuing with the description of the steps summarized in FIG. 6, after the sequencer 118 selects the flow focus map memory 117 and initializes system settings, including adjusting the gain of the receiver 106 and the number of activated transducer elements, control passes to step 232 wherein the sequencer 118 activates transducer elements $t_0-t_3$. After activating transducer elements $t_0-t_3$, the sequencer 118 directs transmit impulse signals in a known manner previously described in the Proudian '097 patent via the transmit bus 140 to transducer elements $t_0-t_3$ which then periodically transmit a total of J ultrasonic excitation signals into the blood vessel. The sequencer 118 also activates transducer elements $t_0-t_3$ for receiving J signal samples which are buffered and transmitted on receive bus 142.

The repetition frequency is maintained at rates up to 163 thousand excitation signals per second in the illustrated embodiment of the present invention. At this rate, the set of J signal samples (where J=256) can be acquired for one of the 64 image regions in less than two thousandths of a second. However, the repetition period can be less than one thousandth, less than one ten-thousandth, or less than one hundred-thousandth of a second.

The very high repetition frequency facilitates a comparison of a first signal sample or set of signal samples and a next signal sample or set of signal samples for an imaged region wherein the relatively static portions of the signal samples (arising from tissue and plaque) are significantly attenuated. The attenuation of the relatively static portions of the signal samples enables the identification of relatively dynamic portions of the imaged region (indicating blood flow).

Figure 12:
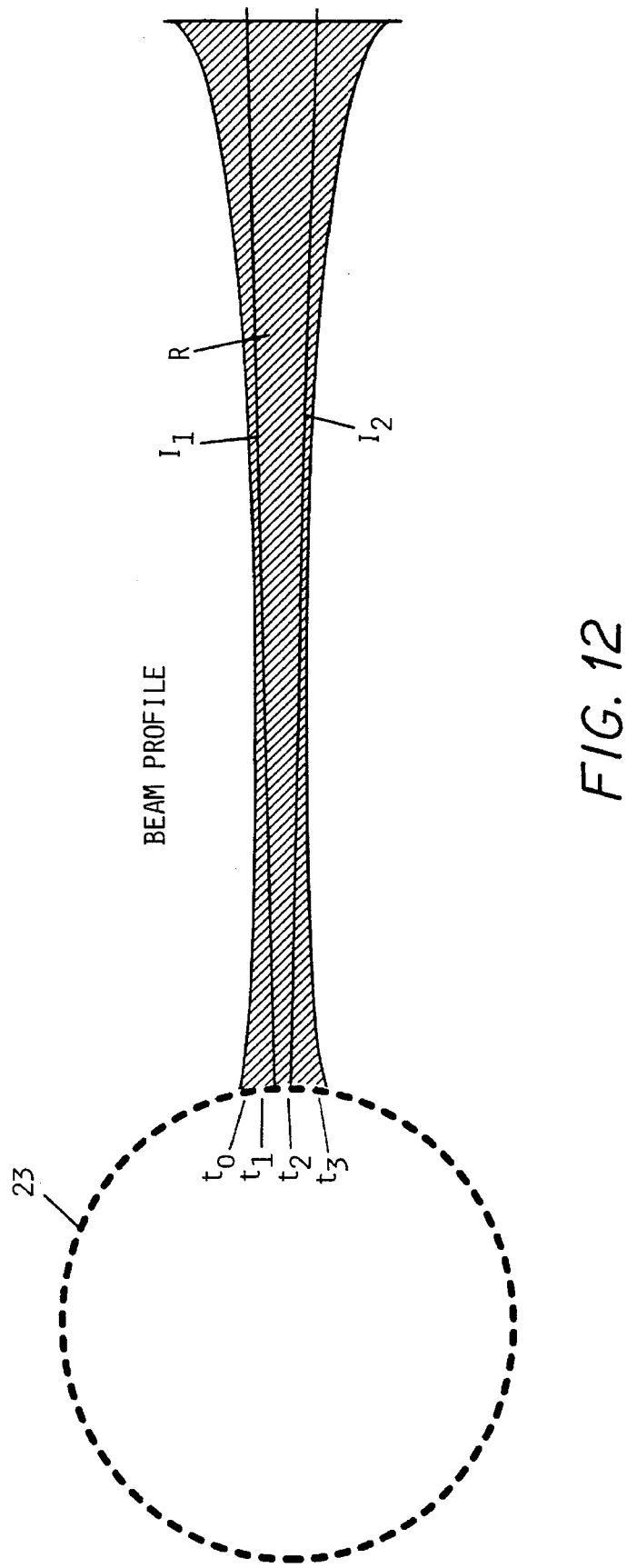
FIG. 12 is a schematic illustration of the beam profile of ultrasonic energy radially propagated from a set of simultaneously activated transducers.

Turning briefly to FIG. 12, a representative beam profile for ultrasonic emissions from four (4) simultaneously activated adjacent transducers ($t_0-t_3$) is depicted. As is known in the art, increasing the size of the aperture at the source (resulting from the simultaneous emission of ultrasonic energy from four (4) adjacent transducers of the 64 transducers), results in an ultrasonic beam profile which is more uni-directional and more focused at farther distances from the source than the beam profile arising from emission of ultrasonic energy by a single one of the 64 transducers. The Beam Profile in FIG. 12 represents the effective portion of the vasculature from which echoes are received by the four (4) activated transducers $t_0-t_3$ immediately after the same four (4) transducers $t_0-t_3$ simultaneously emit an ultrasonic waveform from a cylindrical transducer array 23 having a total of sixty-four (64) transducer elements.

In the illustrated embodiment of the invention, a full-screen flow image comprises 64 image regions. Each one of the 64 combinations of adjacent transducers, taken four at a time, are used to generate a modified echo waveform for a corresponding one of the 64 image regions. FIG. 12 illustratively depicts a region R which comprises one of the 64 image regions of a full-screen flow image. The region R, associated with the activation of transducers $t_0-t_3$, is centered within the Beam Profile and bounded on each side by lines $l_1$ and $l_2$. Of course, alternative embodiments of the present invention may comprise modifications to the number of image regions comprising a full-screen image, the size and shape of the emitting transducer, the size and shape of a beam profile, and the relationship between a beam profile and the image region associated with the beam profile.

Returning to FIG. 6, after the ultrasound imaging system has received the J signal samples in step 232, control passes to step 234 wherein the transmit buffers for transducer elements $t_1-t_4$ are activated via buffer control lines $b_1-b_4$ to periodically transmit J ultrasonic excitation signals into a region of the vasculature from within the blood vessel. The buffer control lines $b_1-b_4$ also activate the receive buffers for transducer elements $t_1-t_4$ for receiving J transduced echo waveforms from the transducer elements $t_1-t_4$ and transmitting the summed current signal on the receive bus 142 as illustrated in FIG. 11 described hereinabove.

The activation of sets of four adjacent transducer elements for emitting J ultrasonic waveforms, receiving by the four adjacent transducer elements J sets of echo waveforms arising from the J emitted ultrasonic waveforms, and shifting by one the activated set of four (4) adjacent transducers is repeated until a total of 64 sets of J signal samples have been received by the signal processor for creating a full-screen flow image. At step 236, the transmit and receive buffers for transducer elements $t_{63}$, $t_0$, $t_1$, and $t_2$ are activated and transmit J ultrasonic waveforms from within the vessel and receive the final set of the 64 total sets of J ultrasonic echo waveforms. The buffered received echo waveforms are summed and transmitted on the receive bus 142.

It should be noted that although, in the illustrated embodiment described above, the same transducer or set of transducers during the normal imaging and flow imaging modes respectively transmit and receive ultrasound energy for a region, other alternative transmit/receive schemes are also possible. For example, in an alternative embodiment, modifications are made to the control scheme and hardware, in a manner that is readily discernable to those skilled in the art, so that a first transducer or set of transducers emit an ultrasonic waveform and a second, distinct, transducer or set of transducers receive the echoes arising from the emitted ultrasonic waveform.

4. Raw Flow Image Data Processing

Figure 7:
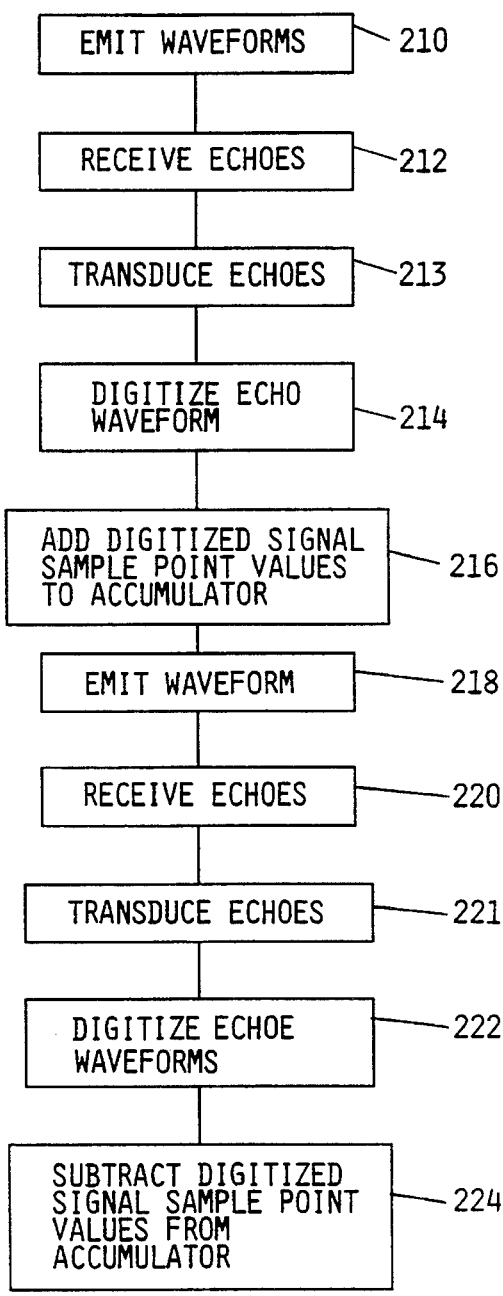
FIG. 7 is a flow chart summarizing the steps for combining the values of two (2) echo waveforms for one radial section of the ultrasound image.

Having described how the echo waveforms comprising the raw flow image data are obtained, attention is now directed to FIG. 7, wherein the steps for an exemplary pattern for combining the values of J digitized signal samples to obtain a modified echo waveform for one image region of the ultrasound flow image are summarized. In the illustrated embodiment of a combination pattern summarized by FIG. 7, the DSA 110 alternates between addition and subtraction after receiving and processing each signal sample from the A/D converter 108. However, the present invention contemplates a multitude of adding and subtracting patterns applied to signal samples which amplify the transduced echo signals from the flowing blood while attenuating transduced echo signals from the static features such as the vessel walls, illustrative examples of which are described hereinafter.

At step 210, the set of four (4) activated transducers emit an ultrasonic waveform signal from within a blood vessel. Thereafter, the ultrasonic waveform signal propagates through a region of the vasculature in accordance with the beam profile schematically illustrated in FIG. 12. While propagating through the region, the ultrasonic waveform signal encounters blood and tissue which results in the creation of ultrasonic echoes.

At step 212, as in the previously described imaging mode, ultrasonic echoes immediately return to the probe assembly 24 from both the blood and the tissue and are sensed by four (4) activated transducers. Next, at step 213, the ultrasonic echoes from the blood and tissue are converted into an electrical current echo waveform by the four (4) activated transducers, buffered by transimpedance amplifiers on board the integrated circuits, summed together into a single electrical current signal on the receive bus 142, and transmitted via a microcable 25 to the receiver 106. The receiver 106 further amplifies and filters the received signals. Thereafter, the resulting amplified and filtered electrical signal is transmitted to the A/D converter 108. Control then passes to step 214.

At step 214, the process of combining the analog echo waveform arising from the ultrasonic echoes, with other echo waveforms for an image region begins with the A/D converter 108 digitizing the amplified echo waveform from the receiver 106. As previously explained in relation to the static imaging mode, the A/D converter 108 generates a signal sample comprising 2048 points from each analog echo waveform arising from the transduced echo signals at the rate of 400 MHz with 8 bits of amplitude resolution. The A/D converter 108 serially transmits the 2048 points of data for the digitized waveform to the DSA 110 and control passes to step 216.

At step 216, a signal sample comprising 2048 digitized points from the A/D converter 108 is added by the DSA 110 to a set of 2048 values stored in the accumulator of the DSA 110 which, as previously described, is capable of performing both addition and subtraction operations. The resulting summed values are re-stored in the accumulator of the DSA 110. Control then passes to step 218.

At step 218, the set of four (4) activated transducers emit a next ultrasonic waveform signal from within a blood vessel. As in step 210, the ultrasonic waveform signal propagates through a region of the vasculature in accordance with the beam profile schematically illustrated in FIG. 12. The ultrasonic waveform signal encounters blood and tissue which results in the creation of ultrasonic echoes.

At step 220, identical in function to step 212, the transducers receive ultrasonic echoes from the blood and tissue in the region arising from the ultrasonic waveform emitted by the set of four (4) adjacent transducers during step 218. Next, at step 221, the ultrasonic echoes are converted by the transducers into an electrical current echo waveform, buffered, summed together on the receive bus 142, and transmitted via the microcable 25 to the receiver 106.

Next, control passes to step 222 wherein the process of combining the analog echo waveform arising from the ultrasonic echoes with other echo waveforms for an image region continues with the A/D converter 108 creating a signal sample comprising 2048 digitized points from the echo waveform received by the receiver 106 during step 220. Control then passes to step 224 wherein the DSA 110, operating in a subtraction mode, subtracts the digitized signal sample from the set of 2048 accumulated point values stored in the accumulator of the DSA 110 at the completion of step 216. The resulting values are restored in the accumulator of the DSA 110.

In the illustrated embodiment of the invention, the exemplary sequence of steps listed in FIG. 7 for alternatingly adding and subtracting transduced echo signals is executed J/2 (128) times on a total of J (256) digitized signals to obtain a modified echo waveform for an image region associated with an activated set of transducers. However, more or fewer digitized signal samples can be processed to obtain the modified echo waveform for the image region.

After performing the steps (of FIG. 7) J/2 times, the DSA 110 transmits the modified echo waveform comprising a set of 2048 accumulated values in the form of 16-bit data to the acoustic frame buffer 112 for storage and subsequent image construction processing.

As previously described in FIG. 6, raw flow image data is obtained by the ultrasonic imaging system for each of 64 image regions of a full-screen flow image. Therefore, the DSA 110 repeats the above-described steps for processing J signal samples for an imaged region a total of 64 times in order to obtain a modified echo waveform for each of the 64 image regions comprising the full-screen flow image.

The steps of an illustrated example of a balanced signal sample addition/subtraction process has been described in conjunction with FIG. 7. However, other sequences for receiving and combining a set of J signal samples arising from echo waveforms from an image region in order to obtain a flow image of the image region are contemplated as falling within the scope of the present invention. A number of such exemplary alternative combining schemes are described herein below.

5. The Filter Characteristics Of The Raw Flow Image Data Processing

The response of the imaging system to objects moving at different speeds within the imaged region is changed by modifying the rate of receiving the set of J transduced signals (which are converted into the J digitized signal samples) and/or by modifying the sequence of substantially balanced additions and subtractions performed by the DSA 110 on the set of J signal samples. However, before discussing the frequency response of blood flow imaging, certain variables bearing upon the frequency response will be defined.

First, the rate at which the transducers emit excitation signals (followed by receiving a set of echo signals) in order to produce the J signal samples is referred to herein as the "repetition frequency" (abbreviated in the drawings as RF). Second, the inverse of the repetition frequency is the "repetition period" (abbreviated in the drawings as RP).

Third, the value M, as used herein, refers to the number of repeated additions or subtractions performed by the DSA 110 in processing the set of J signal samples. In the illustrated example of a combination scheme summarized in FIG. 7, M equals one (1). However, in an alternative example where M equals two (2), the DSA 110 performs a series of two (2) addition operations, followed by a series of two (2) subtraction operations, then two (2) additions, etc., until a total of J signal samples have been processed by the DSA 110. The values of J and M should be selected such that the addition and subtraction operations on the signals are substantially balanced to ensure that static portions of the signal samples are substantially attenuated in comparison to the dynamic portions in the resulting modified echo waveform for an image region.

Figure 8A:
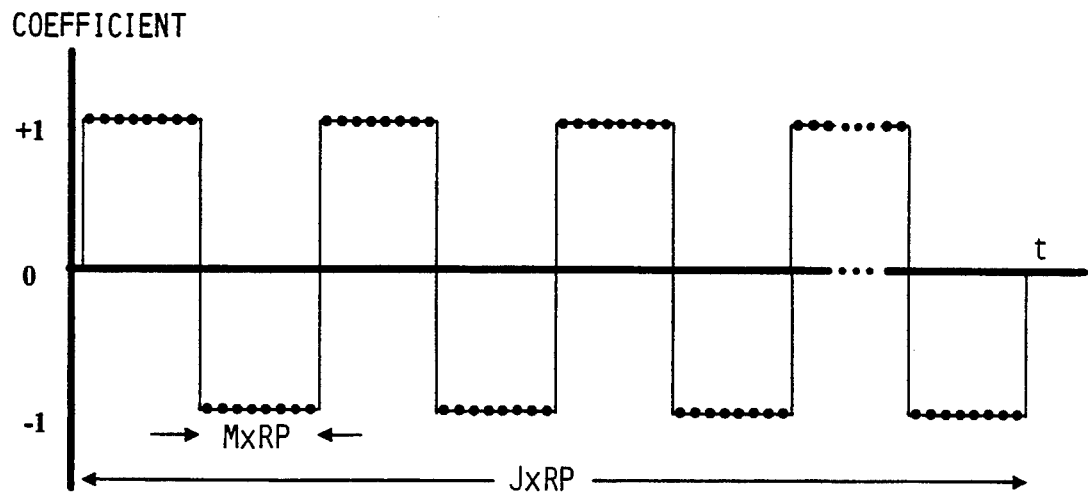
FIG. 8a is an illustration of a time series square wave for modulating the received echo waveforms in one exemplary implementation of flow image filtering.
Figure 8B:
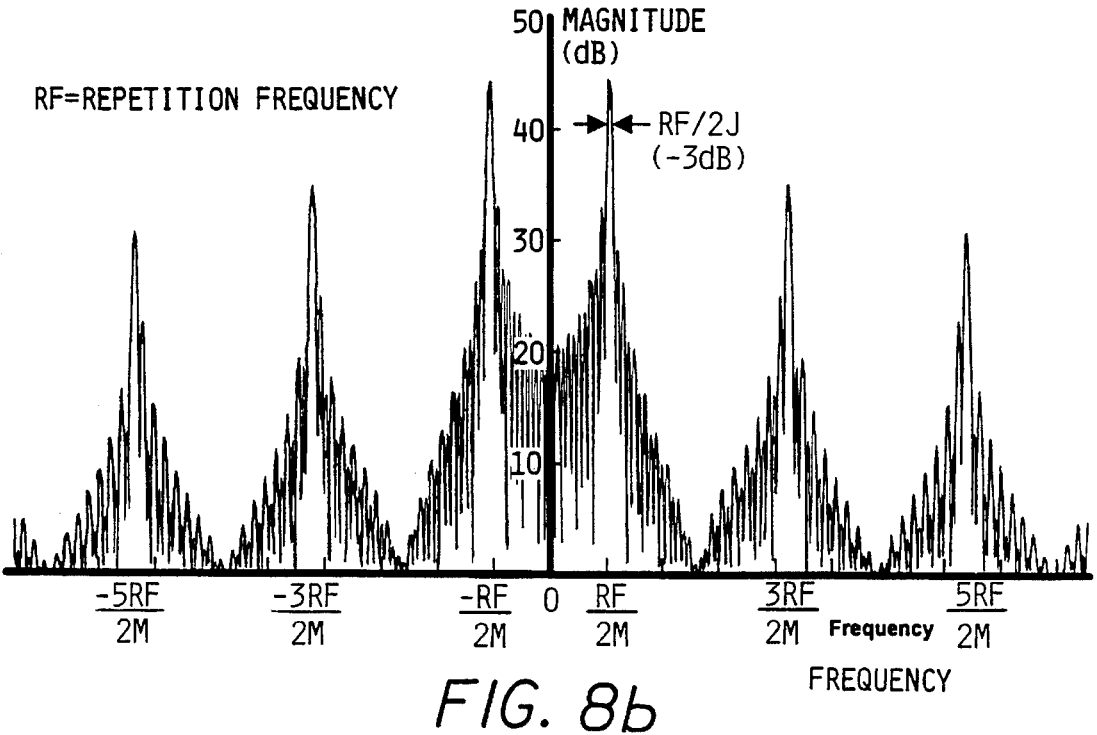

Turning to FIGS. 8a and 8b, an example is provided of a filter frequency response for an exemplary signal sample processing sequence. The bi-polar square wave in FIG. 8a represents, in the time domain, the modulation of the J signals (converted into the J signal samples) by means of the sequence of additions and subtractions performed on the J signal samples. The length of each positive or negative segment of the square wave depicted in FIG. 8a is equal to M (the number of repeated additions or subtractions of signal samples) times the repetition period (RP). Furthermore, the total length of the square waveform, representing the acquisition of J sets of transduced signals (for creating the J signal samples), equals J times the repetition period (RP). For a repetition rate of 163 thousand repetitions per second, the acquisition period for the J signal samples is on the order of thousandths of a second. However, the acquisition period may be increased or decreased as long as the total acquisition time is less than a maximum time period. The maximum time period is that in which the tissue in an imaged region of a vasculature remains in a substantially fixed position. As a consequence, when the J signal samples are combined, the combined signal for the portion of the imaged region primarily containing tissue is substantially attenuated in comparison to the combined signal for the portion of the imaged region primarily containing flowing blood.

FIG. 8b illustrates the frequency response of the sampling sequence obtained from the Fourier transform of the time domain series of additions and subtractions of the J signal samples depicted in FIG. 8a. The Fourier transform of FIG. 8a illustrated in FIG. 8b demonstrates that the peaks of the frequency response for the square wave sampling scheme illustrated in FIG. 8a occur at frequencies represented by $$\text{Center Frequency} = \pm \frac{\text{Repetition Frequency}}{2M} \quad (1)$$

Therefore, in accordance with equation (1), increasing M or decreasing the Repetition Frequency tends to decrease the Center Frequency.

Furthermore, to a first order approximation, the −3dB bandwidth of the primary peaks at the Center Frequency is approximated by the equation:

$$-3\text{dB bandwidth} = \frac{\text{Repetition Frequency}}{2J} \quad (2)$$

Therefore, in accordance with equation (2), increasing the number of combined signal samples J or decreasing the Repetition Frequency narrows the −3dB bandwidth.

Continuing with the Frequency Domain response illustrated in FIG. 8b, due to the square wave filter sampling, harmonics are generated at odd, whole number, multiples of the Center Frequency. In addition, since the time series sampling is effectively a boxcar sampling of the data, each odd frequency bandpass shape at baseband and at each odd harmonic is effectively a (Sin X)/X response as can be seen in FIG. 8b. The mirror image frequency response in the negative frequency spectrum illustrates the sensitivity of the filter to both forward and reverse motion of the blood without discrimination.

Applying the frequency response characteristics of the add/subtract sequences described above with respect to FIGS. 8a and 8b to blood flow imaging. A value for M is preferably selected which amplifies the (relatively dynamic) blood echo signals while substantially attenuating the (relatively static) tissue echo signals. Alternating addition and subtraction operations after each signal sample (M=i), as illustrated in FIG. 7, when the repetition frequency equals 163 thousand excitations/receives per second, produces an image of fast changing portions of the imaged region (i.e. fast flowing blood). Alternating addition and subtraction operations after every three, four or more signal samples (M≧3) increases the sensitivity of the flow imaging mode to less quickly changing portions of signal samples arising from slower moving blood or slow moving tissue.

In order to capture (for flow imaging) the echo signals from slower moving blood, the value for M is increased. However, a drawback to increasing the value of M, thus increasing the size of strings of consecutive repeated addition or subtraction operations, is that the signal response of the imaging system to slow moving tissue increases. An increased signal response to moving tissue confounds blood flow imaging and therefore limits the maximum value of M for a given repetition frequency.

Though not specifically illustrated in the drawings, a user of the ultrasonic imaging system is preferably provided access to controls for re-programming the addition/subtraction sequences performed by the DSA 110 in order to modify the filter characteristics of the imaging system. The specified addition and subtraction sequence is stored by the sequencer 118. The sequencer 18 then transmits control signals to the DSA 110 causing the DSA 110 to carry out the specified addition and subtraction sequence on a set of J signal samples.

By modifying the filter characteristics, the user enables the ultrasound imaging system to provide the best possible flow image under a specific circumstance. This is especially important in blood flow imaging since the characteristics of blood flow and tissue movement vary considerably within the vascular system of the body. The steps of the method summarized in the flow chart shown in FIG. 7, as well as the number of iterations of those steps, are altered in a straightforward manner in accordance with the modified addition/subtraction sequences submitted by a user to the sequencer 118 for application by the DSA 110 upon J signal samples.

6. Processing The Imaging Signals To Obtain A Video Image

Continuing with the description of step 202 of FIG. 4, the sequencer 118 transmits a control signal on line 121 to the switch 115 to connect the flow focus map memory 117 to the sequencer 118 in order to provide proper control signals to the cross-point switch 114, multiplier 119 and Wallace adder 120 in order to calculate image values for a set of 64 distinct imaging vectors. The flow focus map memory 117 defines all of the delays and weightings necessary to calculate, in a known manner, point values for the imaging vectors from the 64 modified echo waveforms stored in the acoustic frame buffer 112. In the illustrated embodiment of the present invention, reconstructive focusing is not used, and data is passed through the Wallace adder 120 without being added together with other sets of weighted data, and therefore no further focusing is implemented by the Wallace adder 120. This is accomplished by loading zero values into nine of the ten weighting elements of the multiplier 119, and only a single weighting element receives a non-zero weighting value. Since reconstructive focusing is not used, the 64 different combinations of activated adjacent transducers (summarized by the steps of FIG. 6) result in a set of 64 distinct imaging vectors.

In order to generate a full-screen flow image, each one of the set of 64 distinct imaging vectors (corresponding to the 64 image regions) is mapped, on average, into 27 distinct imaging vectors of the 1760 separate imaging vectors presented to the angle dependent sample rate converter 124 for purposes of assigning pixel values for the flow image in a 440 by 440 pixel video system. The actual number of separate imaging vectors into which a one of the 64 distinct imaging vectors is mapped is determined by the number of pixels on the edge of a portion of a display screen of the video display 28 corresponding to an imaged region of the vasculature associated with the one of the 64 distinct imaging vectors.

The set of 64 distinct imaging vectors is transmitted from the Wallace adder 120 to the digital rectifier and filter 122 for processing in a manner previously described above in conjunction with the hardware description of the ultrasonic imaging system. The rectified and filtered image data is thereafter transferred to the angle dependent sample rate converter 124. The angle dependent sample rate converter 124 converts the vector values of the 1760 imaging vectors expressed in polar coordinates into a set of 1760 converted vector image values expressed in terms of a Y coordinate and an angle ], and the 1760 converted imaging vectors in the Y/] buffer 126 are transferred and assigned by the concentric squares generator 128 into nearest corresponding pixel locations in the 440 by 440 pixel video system in a manner described in the Proudian et al. '097 patent incorporated herein by reference. The flow image data corresponding to the pixel locations is then transmitted to the video system 130. The video system 130 colorizes the flow image pixel data for pixel values which meet or exceed a threshold value.

Colorizing the flow image pixel data enhances the contrast between the dynamic portion of the image associated primarily with the blood flow, and the static portion of the image associated primarily with the vessel wall and tissue. In the illustrated embodiment of the present invention, the video system assigns the color red to the flow image pixel data; however, other suitable alternative display schemes would be known which may be used to enhance the contrast between the tissue and blood flow in a composite image.

7. Storing The Flow Image

Continuing with the description of FIG. 4, after the pixel values are calculated for the ultrasound image (at step 202), control passes to step 203. At step 203, the resulting colorized pixel values for the image acquired while the ultrasound imaging system operates in the flow imaging mode are selectively transmitted via the video system 130, through the switch 3 (controlled via line 123 from the sequencer 118), and stored within the flow pixel memory 132a. Thereafter, control passes to step 204 wherein the ultrasound imaging system of the present invention generates a composite image based upon the pixel data from the image pixel memory 132b and the colorized pixel data from the flow pixel memory 132a.

8. Generating A Composite Image

In the illustrated embodiment of the present invention, the imaging system (at step 204) creates the composite image by summing the pixel values from the image pixel memory 132b with the corresponding pixel values from the flow pixel memory 132a by means of the summing circuit 133.

The summing circuit 133 receives a single pixel value from each of the pixel memories 132a and 132b (corresponding to a same location on the display screen) and adds the two signals to obtain a value for a pixel on the display screen. This summing procedure is repeated for each pixel location on the display screen in order to obtain the composite image.

9. Displaying A Composite Image

Continuing with the description of the steps of FIG. 4, control next passes to step 205 wherein the composite image is displayed upon a video display terminal 28. In accordance with one aspect of step 205, the summed pixel data is first transmitted to the gamma correction lookup table 134 where the pixel data from the summing circuit 133 is processed in a known manner. The corrected pixel data is next transmitted to the D/A converter 135 wherein the corrected pixel data is used to control a video display 28 for displaying a composite image of the blood vessel comprising a black-and-white image of relatively static features and a colorized image of blood flow and other dynamic features. Though the step of displaying a composite image is presented as the final step in FIG. 4, it will be appreciated that the step of displaying a composite image based upon data stored in the flow pixel memory 132a and image pixel memory 132b may occur at any time after valid image data has been stored in the pixel memories 132a and 132b. Furthermore, the refreshing of the displayed image may occur several times for every time the pixel memories 132a or 132b are loaded with new data.

10. Laboratory Testing Of The Illustrated Embodiment

In testing the above-described ultrasound imaging system and method utilizing the alternating signal sample combining scheme represented by FIG. 8a, an imaging catheter was connected to the imaging system, and the imaging mode was checked using standard image focus maps. The catheter was placed in a plastic tube and an image was made.

Thereafter, the system was switched to the flow imaging mode described hereinabove. A volume of microballoon loaded water was injected past the imaging catheter within the plastic tube using a syringe. During repeated injections, the alternating addition/subtraction sequence (i.e., the value of M) was increased by powers of two. For example, the following sequences were performed by the DSA 110.

```
+-+-+-+-+-+-+-...
++--++--++--++...
++++----++++----...
++++++++--------++++++++...
```

Furthermore, the speed of flow of the loaded water was varied in order to test the sensitivity of each sequence to varying velocities of flow. This process was repeated with fresh lamb's blood and more sensitive transducers, such as those described in Eberle et al. pending U.S. patent application Serial Number 08/012,251 which is incorporated herein by reference.

With the microballoon suspension, flow was clearly visible within the confines of the plastic tube. With the transducer eccentrically placed in the tube, the flow pattern corresponded directly with the position of the lumen. Due to signal saturation, the relatively large echoes from the plastic tube were not fully canceled in the flow image and were visible around the flow pattern.

Using the lamb's blood as the flow medium, insufficient sensitivity was obtained using a standard transducer catheter. Instead, a higher power transducer catheter was used of the type described in the Eberle et al. U.S. application 08/012,251, with about 30dB more sensitivity. For this transducer, the lower level backscatter from the red blood cells was clearly visible and enabled the imaging of the position of the lumen in the plastic tube.

These experiments have demonstrated the feasibility of extracting the information of flow from a backscattering medium, such as blood. Colorization and overlay onto a two-dimensional cross-sectional tissue image will help identify regions of blood flow previously unclear in past imaging techniques and apparatuses.

E. Alternative Embodiments Of The Invention

1. Magnitude Modulatinq Filter Sequences

By alternatingly adding and subtracting signal values, the DSA 110 effectively modulates the input signal values by a plus or minus one value equivalent to a bi-polar square wave (illustratively depicted in FIG. 8a). However, in an alternative embodiment of the invention, the signal processor 30, in addition to performing a sequence of addition and subtraction on a set of J signal samples for an image region (in accordance with a specified M value), modulates the magnitude of ones of the set of J signal samples by applying a sequence of non-unitary coefficients to the set of J signal samples.

Figure 9A:
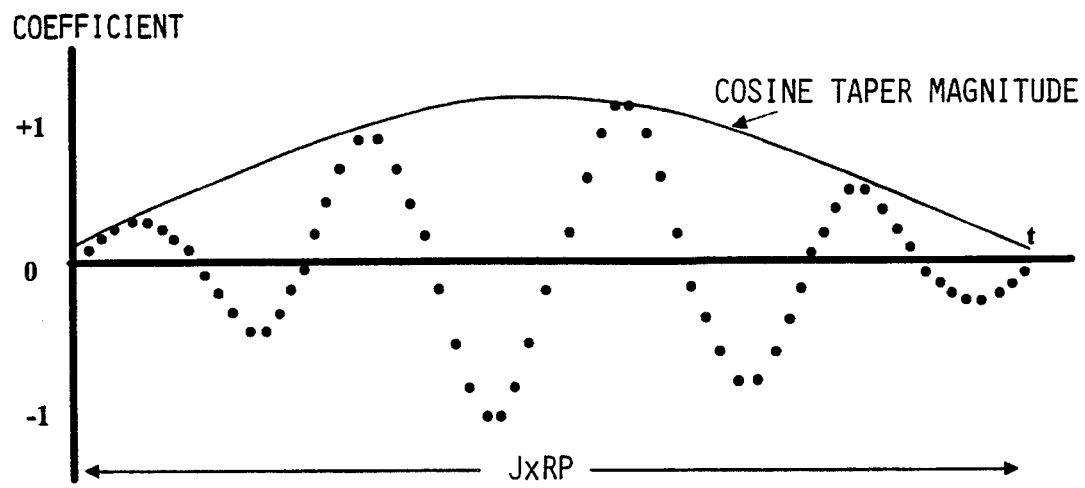
FIG. 9a is an illustration of another illustrative time series for modulating the received echo waveforms in another exemplary implementation of flow image filtering.

In an alternative modulation pattern shown in FIG. 9a, instead of unitary coefficients, which define a square wave, the balanced coefficients are selected such that the coefficient values follow a sine wave pattern within a cosine taper magnitude envelope. The sine wave pattern removes harmonics in the frequency domain as long as no distortion is introduced. In addition, the time series of J samples is windowed with a standard function such as a Cosine taper, Gaussian, Hamming, etc. in order to shape the bandpass characteristics, change the bandwidth, and reduce sidelobes.

Figure 9B:
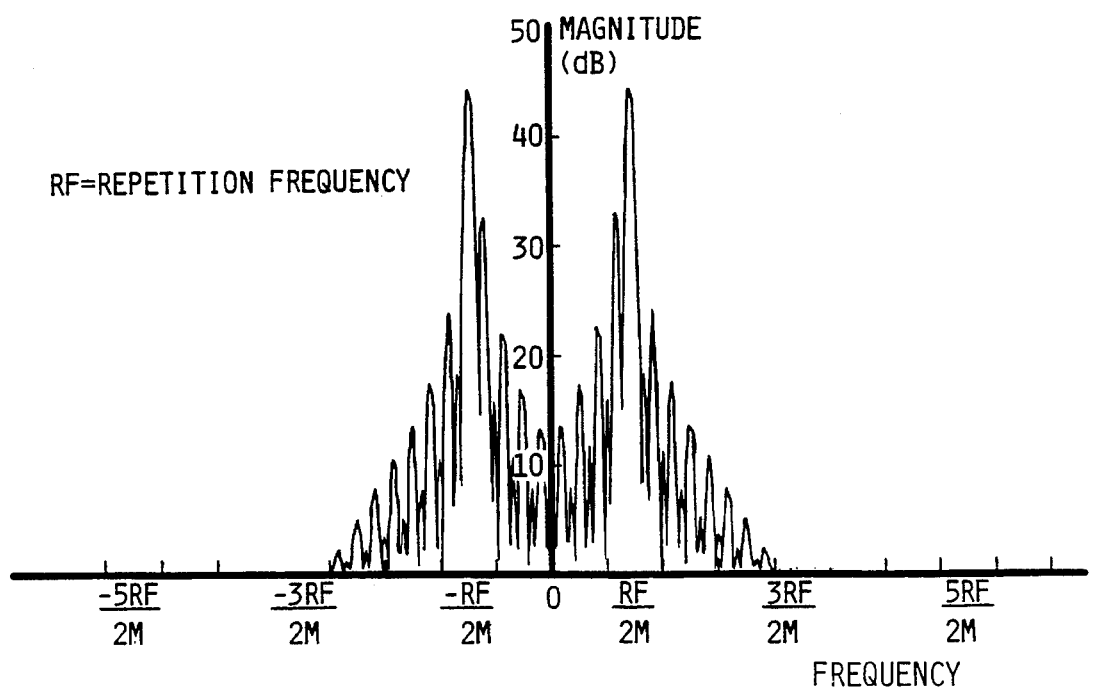

The effect of modulating the J received signals by a sine wave within a cosine taper envelope is shown in FIG. 9b. Thus it will be appreciated by those skilled in the art in view of these examples of filters that the filter characteristics of this imaging method can be further tailored, through amplitude modulation of the signals, to improve contrast between relatively static and relatively dynamic features in a vessel in a variety of flow imaging situations.

In carrying out non-unitary modulation of received signals, the modulation of the signal should be such that the addition and subtraction operations are substantially balanced. In other words, the series of modulation coefficients applied to the signal samples which are added by the DSA 110 should be equivalent to the series of modulation coefficients applied to the signal samples which are subtracted by the DSA 110 for the J signal samples for an image region. The balanced coefficients result in the attenuation of the portions of the combined signal samples attributable to echo signals caused by stationary features (e.g., tissue) in an image region.

Figure 10:
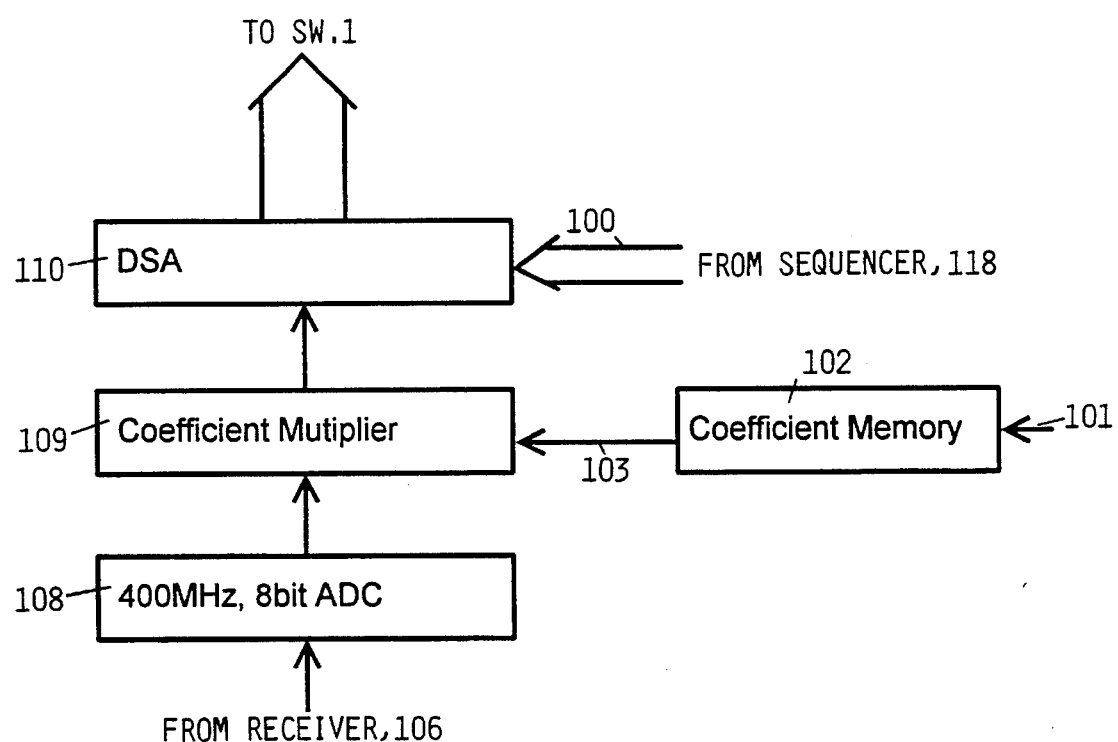
FIG. 10 is a block diagram of a portion of the signal processor of FIGS. 3a and 3b showing the modifications to the signal processor in order to carry out filtering by modulating the received echo signals with the exemplary time series modulation sequences illustrated in FIGS. 9a and 9b.

Turning to FIG. 10, modulation of the echo signals is achieved by means of a coefficient multiplier 109 inserted between the A/D converter 108 and the DSA 110 (of FIG. 3a). The modulation coefficient sequences applied by the coefficient multiplier 109 to the echo signals are provided by a coefficient memory 102. Address lines 101 from the sequencer 118 select the coefficient sequences provided by the coefficient memory 102 to the coefficient multiplier 109 on data lines 103.

2. Applying Multiple Filter Sequences To Siqnals From A Same Imaqe Region

Figure 13:
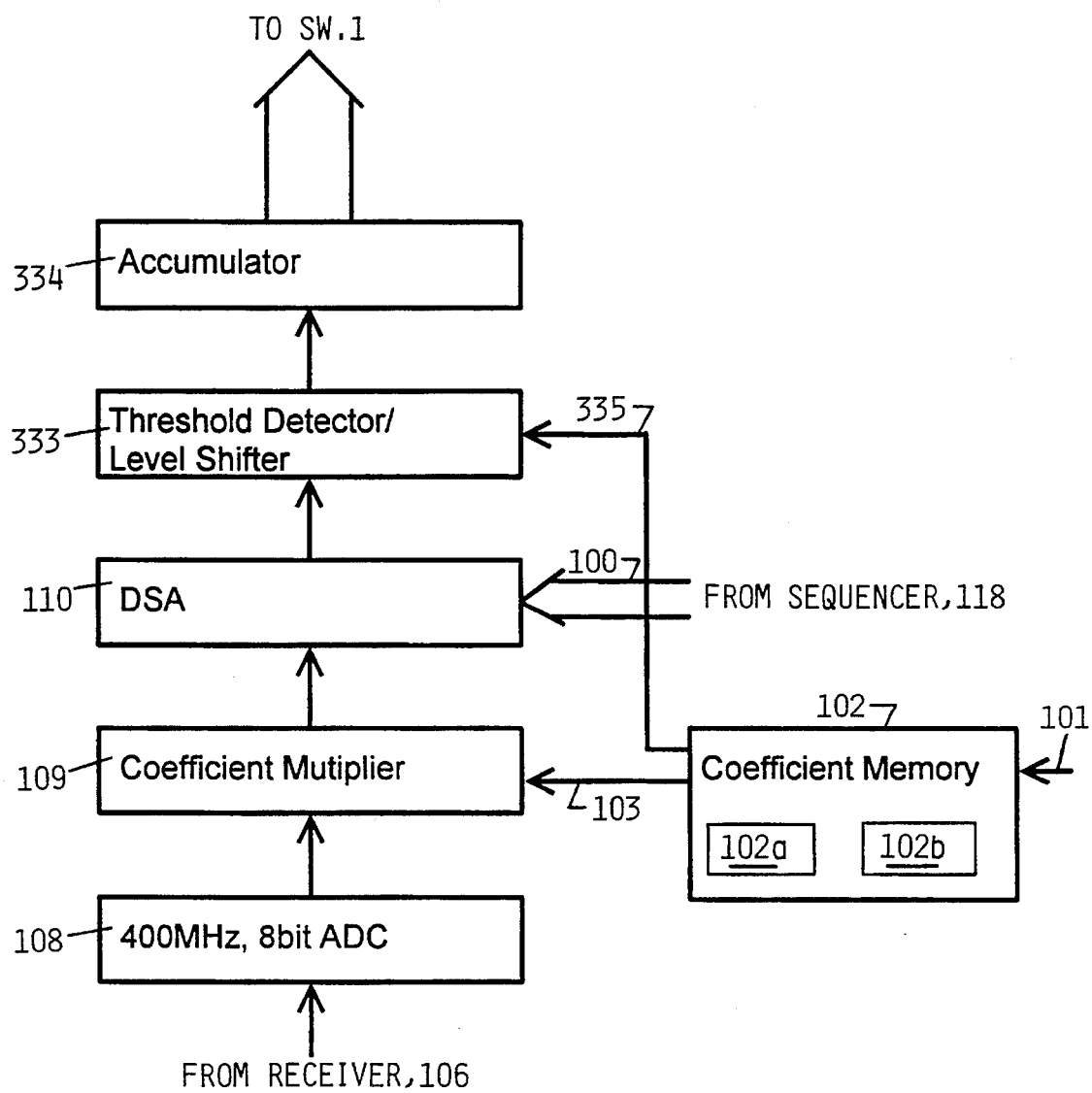
FIG. 13 is a schematic diagram showing a modified portion of the image processor illustrated in FIG. 3a to facilitate applying a plurality of filter waveform sequences to a set of echo waveforms for a region.
Figure 14:
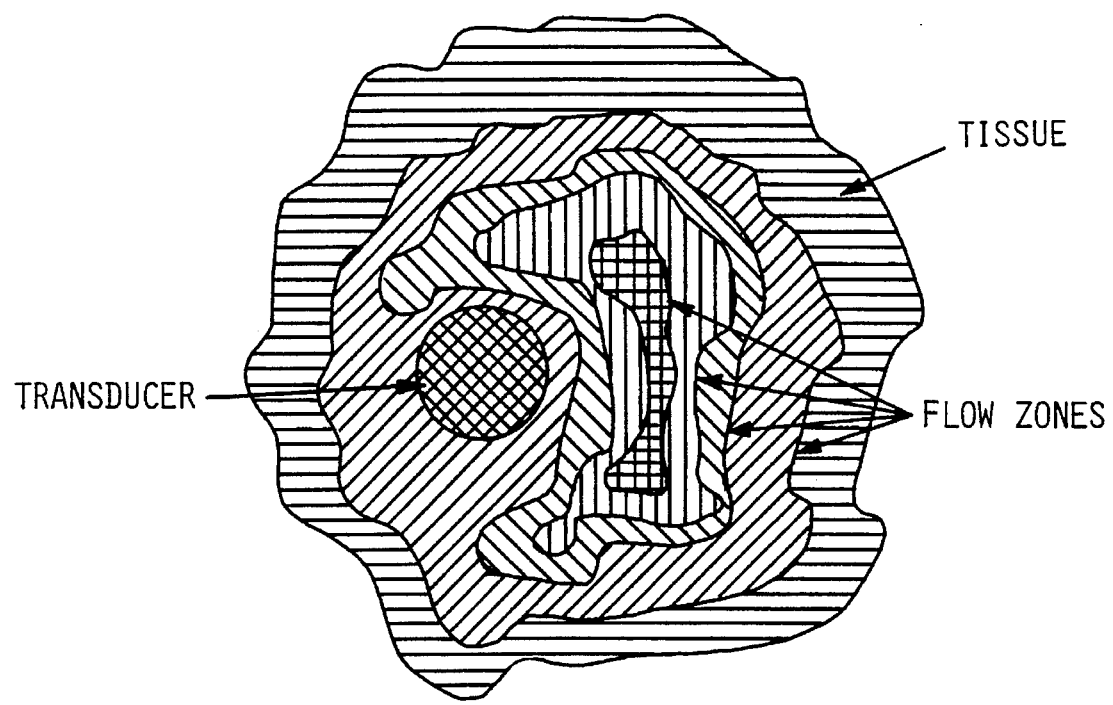
FIG. 14 is an exemplary composite flow image of a cross-section of a blood vessel including four distinct flow zones.

The frequency response of the combined echo waveforms (signal samples) is proportional to the flow speed of the blood. Thus, in another alternative embodiment of the present invention, a set of N filters having primary frequency sensitivity at N different frequencies provide N sets of flow image data for creating a composite blood flow image having N different display modes (e.g., colors or intensities) for distinguishing between up to N flow zones having up to N different ranges of blood flow speed. A schematic diagram is provided in FIG. 13 showing a modified portion of the image processor illustrated in FIG. 3a to facilitate carrying out the alternative flow imaging scheme. An exemplary composite flow image is illustratively depicted in FIG. 14 for a system where four filters are provided (i.e. N=4). The resulting flow image of FIG. 14 is characterized by a cross-sectional image showing the transducer, the tissue, and four distinct flow zones characterized by four different blood flow speeds.

Turning to FIG. 13, the modifications to the signal processor in FIG. 3a comprise the insertion of a coefficient multiplier stage 109 which receives digitized signal samples from the A/D converter 108 and modifies the signal samples in accordance with multiplier values provided on data lines 103 from a first portion 102a of the coefficient memory 102. The selection of multiplier values from the first portion 102a is governed by signals transmitted by the sequencer 118 on address lines 101.

The modified signal samples are transferred from the coefficient multiplier 109 to the DSA 110. The modified signal samples are combined by the ALU's of the DSA 110 with an accumulated value stored in the DSA 110 in accordance with an add/subtract mode signal transmitted by the sequencer via the control bus 100. After the set of J signal samples are combined in the DSA 110, the combined signal is transferred to a threshold detector/level shifter 333.

The threshold detector/level shifter 333, under the control of a second set of signals provided by a second portion 102b of the coefficient memory 102 via line 335, filters and normalizes the digitized values from the DSA 110. The values for the threshold and the shift level transmitted from the second portion 102b are determined by signals transmitted by the sequencer 118 on address lines 101. The threshold detector/level shifter 333, in a known manner, sets to zero the values of the set of values representing the combined signal from the DSA 110 which do not meet a specified minimum magnitude (provided by the coefficient memory 102). The threshold detector/level shifter 333 scales the values which exceed the specified minimum magnitude to a non-zero value, in a known manner, in accordance with a level provided by the coefficient memory 102. The non-zero, level shifted values are thereafter stored in an accumulator 334.

Figure 15:
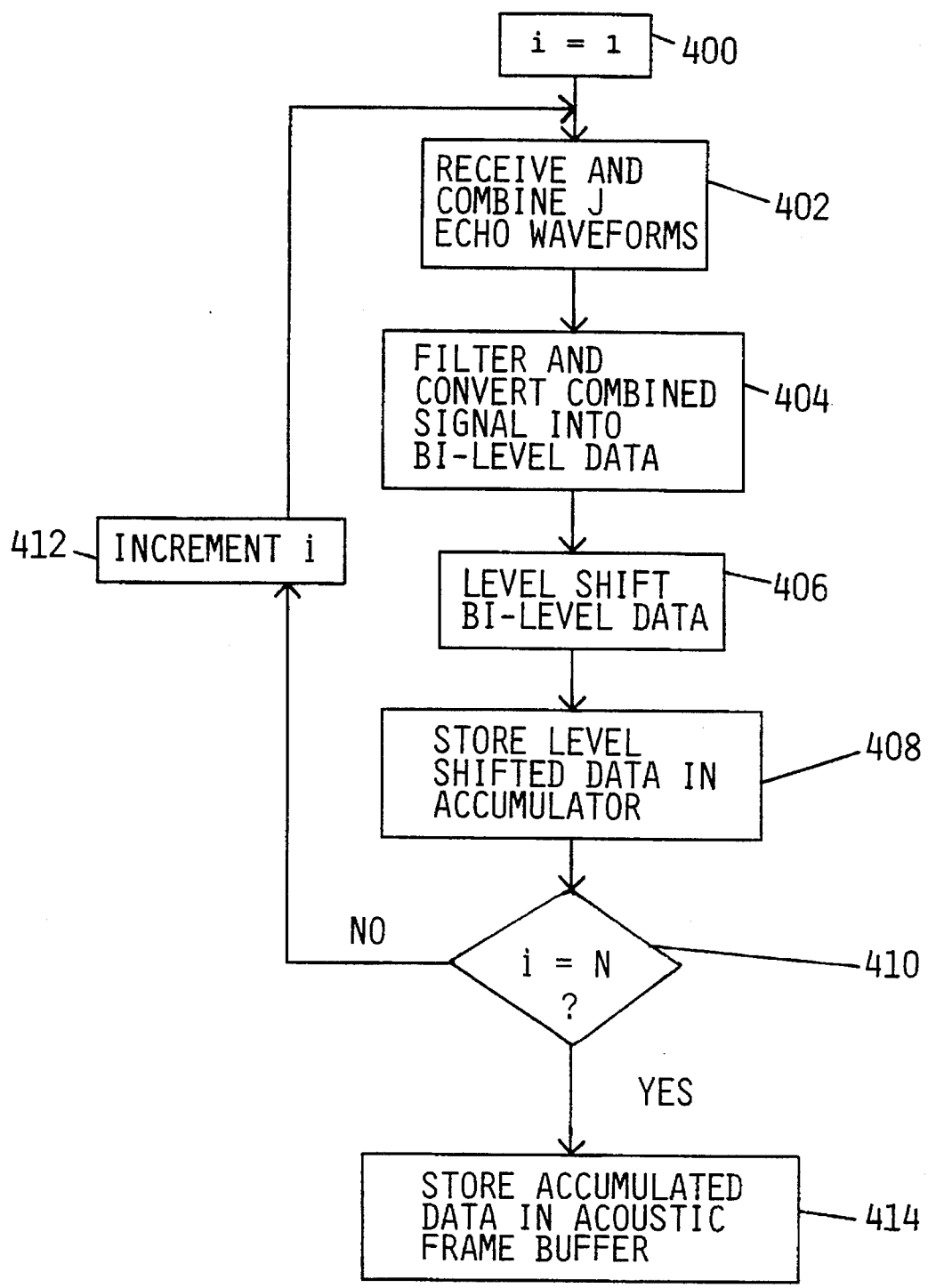
FIG. 15 is a flow chart summarizing the steps for obtaining filtered flow image data for a region of a vasculature from a plurality of bandpass filters.

The steps for obtaining filtered image data from a plurality of bandpass filters are summarized in FIG. 15. These steps will be described in conjunction with the exemplary waveforms and frequency response curves provided in FIGS. 16a–b, 17, 18a–d, 19a–d, and 20. The image processing system makes N passes through the steps 402–410 summarized in FIG. 15, one pass per applied filter waveform. In accordance with the alternative embodiment of the present invention having four (4) filters, the processor passes through the steps of FIG. 15 a total of four (4) times. It is assumed that the value of J is selected such that the blood flow rate remains substantially constant while the signal samples are acquired for processing using the N filter waveforms. Furthermore, four filters have been chosen for purposes of illustrating the flow rate imaging aspect of the invention. Other numbers of multiple filters may also be utilized to cover a region of interest.

At step 400, a counter i is set to one (1). Control passes to step 402 wherein J sets of digitized signal samples are processed by the coefficient multiplier 109 and the DSA 110 in accordance with the filter characterized by a waveform $W_1$ illustrated in FIG. 16a. The frequency response of the filter waveform $W_1$ is generally illustrated as response curve $C_1$ in FIG. 16b, and has a peak frequency response at $F_1$. Combining a set of J signal samples from echo waveforms (such as the echo waveform graphically illustrated in FIG. 17 having a relatively dynamic portion D from the blood and a relatively static portion S from the tissue) in accordance with filter waveform $W_1$ results in a combined signal wherein only a portion of the dynamic blood signal is detected as illustratively shown in FIG. 18a.

Figure 18A:
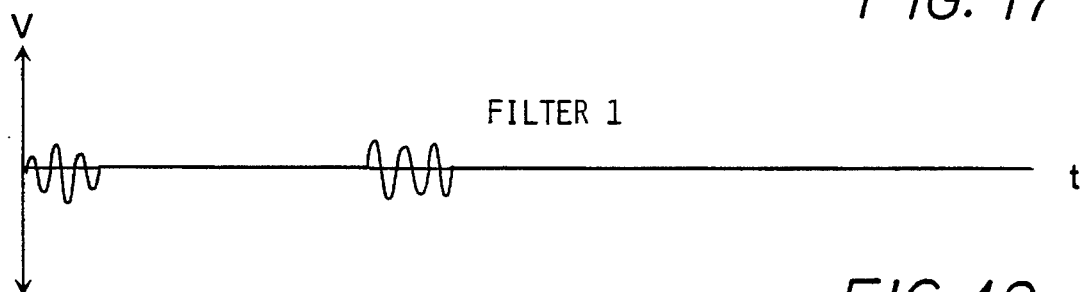
FIGS. 18a, 18b, 18c, and 18d are each a graphical illustration of partial modified echo waveforms resulting from the application of each of the four time series filter waveforms of FIG. 16a to a set of echo waveforms for a region having static and dynamic portions as illustrated in the exemplary echo waveform in FIG. 17.
Figure 19A:
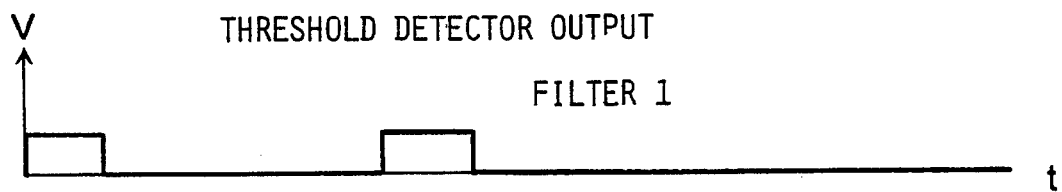
FIGS. 19a, 19b, 19c, and 19d are each a graphical illustration of the output of a threshold detector stage having as its input the data represented by the signals of FIGS. 18a, 18b, 18c and 18d, respectively.

The DSA 110 transfers a set of values for the J combined signal samples, graphically illustrated by means of the partial modified echo waveform in FIG. 18a, to the threshold detector/level shifter 333. Next, at step 404, a threshold detector portion of the threshold detector/level shifter 333 converts the set of digital values graphically illustrated in 18a, in a known manner, into a set of bi-level data of the type graphically illustrated in FIG. 19a. Control then passes to step 406 wherein the waveform values illustrated in FIG. 19a are level shifted by the threshold detector/level shifter 333 in accordance with a level value transmitted on line 335 from the coefficient memory 102. The level shifted partial modified echo waveform corresponding to filter waveform W1, is assigned the lowest level.

Next, at step 408, the set of values for the level shifted partial modified echo waveform corresponding to filter waveform $W_1$ is stored in the accumulator 334.

Figure 18B:
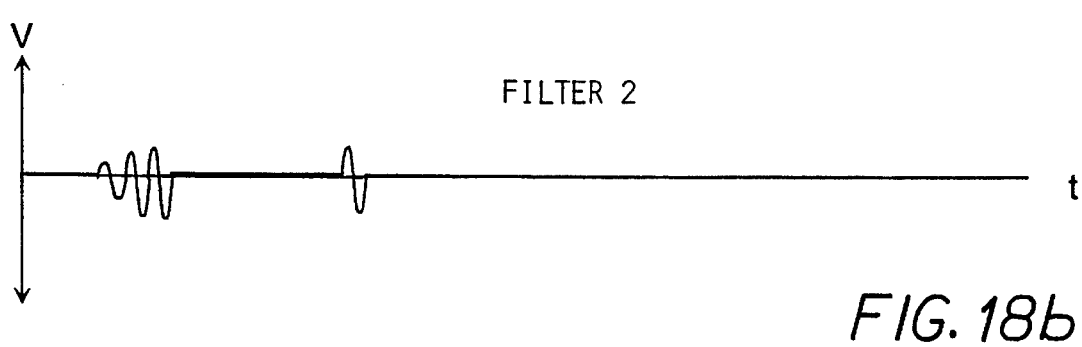
Figure 18C:
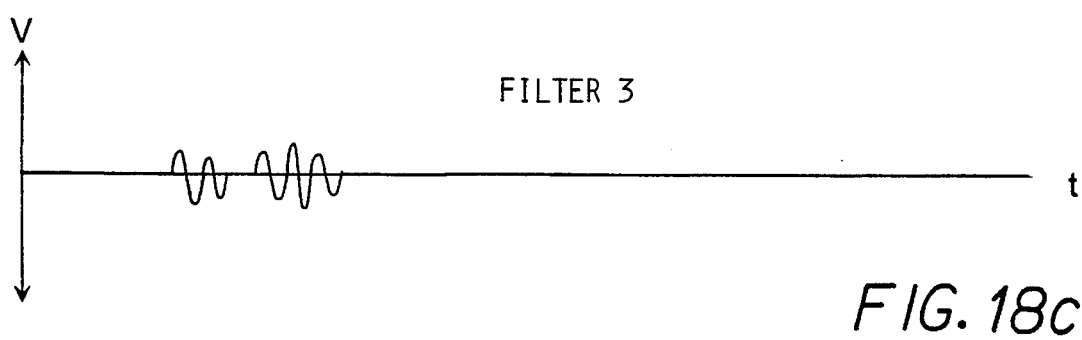
Figure 18D:
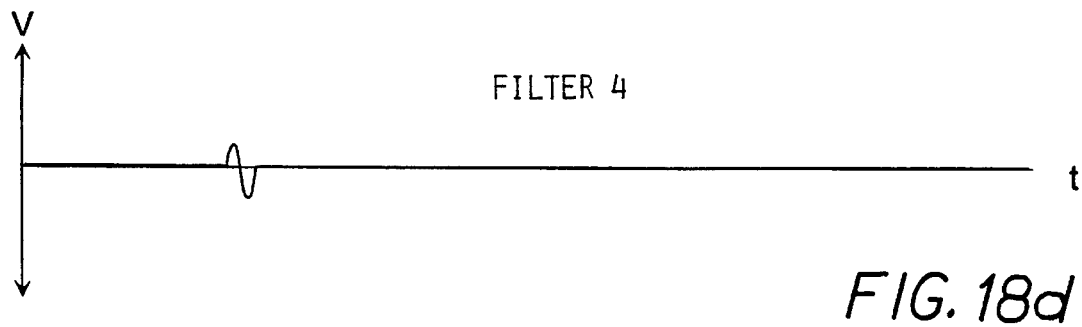
Figure 19B:
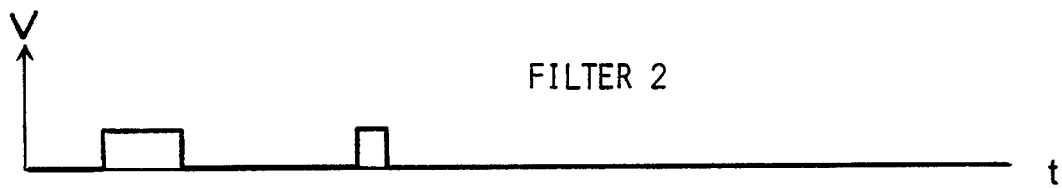
Figure 19C:
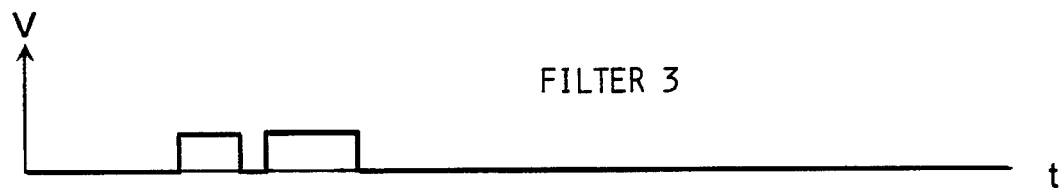
Figure 19D:
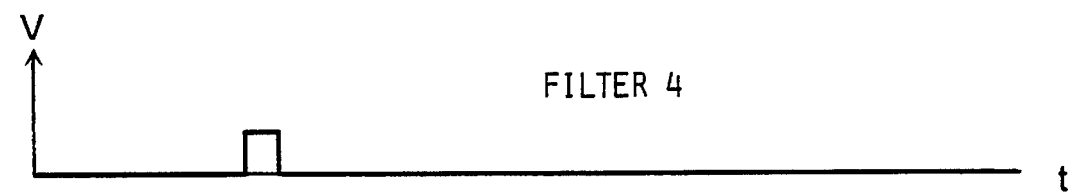

Next, at step 410, if the imaging system has not applied each of the N signal filter waveforms W for a region, then control passes to step 412 wherein the counter i is incremented by one and the filter waveform $W_2$ having a peak frequency $F_2$, is applied to a set of J digitized signal samples in accordance with step 402 to obtain the partial modified echo waveform illustratively depicted in FIG. 18b. The modified frequency response provided by applying $W_2$ is achieved by modifying one or more of the variables (i.e., M or RF) contained in Equation (1) above. In accordance with step 404, the partial modified echo waveform illustrated in FIG. 18b is processed in the manner described above with respect to the filter waveform W1, to obtain the bi-level waveform shown in FIG. 19b. Thereafter, the bi-level waveform illustrated in FIG. 19b is level shifted (step 406) and stored in the accumulator 334 (step 408).

In the illustrated alternative embodiment, the nonzero data associated with each filter waveform $W_i$, does not overlap with the non-zero data associated with the other filter waveforms. In actuality there is overlap of non-zero data for a particular region. The overlap is resolved by overwriting previously stored non-zero data with the non-zero data associated with the most recently applied filter waveform W. Therefore, if non-zero data associated with filter waveform $W_2$ overlaps non-zero data associated with filter waveform $W_1$ which was previously stored in the accumulator 334, then the non-zero data associated with $W_2$ replaces the overlapping non-zero data associated with filter waveform $W_1$.

Figure 16A:
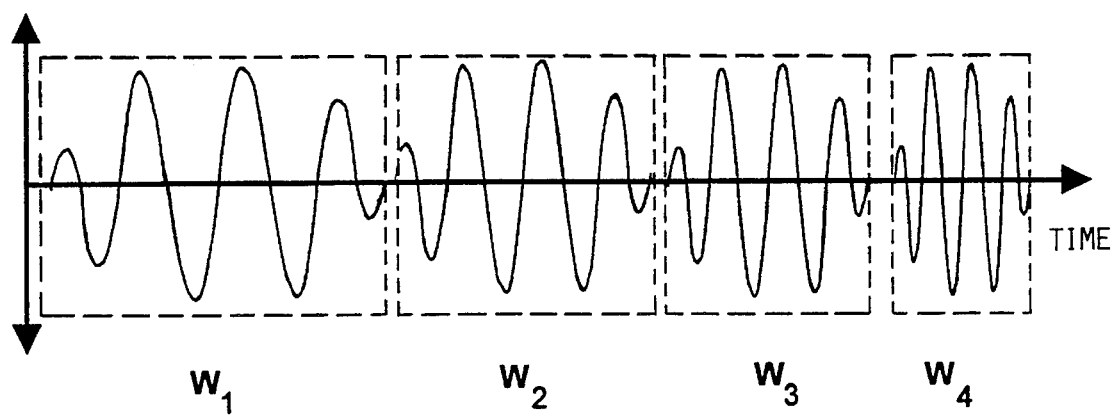
FIG. 16a is a graphical illustration of a set of four time series filter waveforms for combining the received echo waveforms in another exemplary implementation of flow image filtering.

The image processing system re-executes the afore-described control loop summarized in FIG. 15 until each of the filter waveforms $W_i$, illustratively depicted in FIG. 16a, having a corresponding peak frequency response $F_i$, has been applied to a set of J signal samples for a selected region of the vasculature (where i=1 to 4 in the illustrated alternative example). The resulting modified partial echo waveforms for each of the applied filters is shown in FIGS. 18a, 18b, 18c, and 18d, and the corresponding threshold detector output waveforms are illustratively depicted in FIGS. 19a, 19b, 19c, and 19d respectively.

Figure 20:
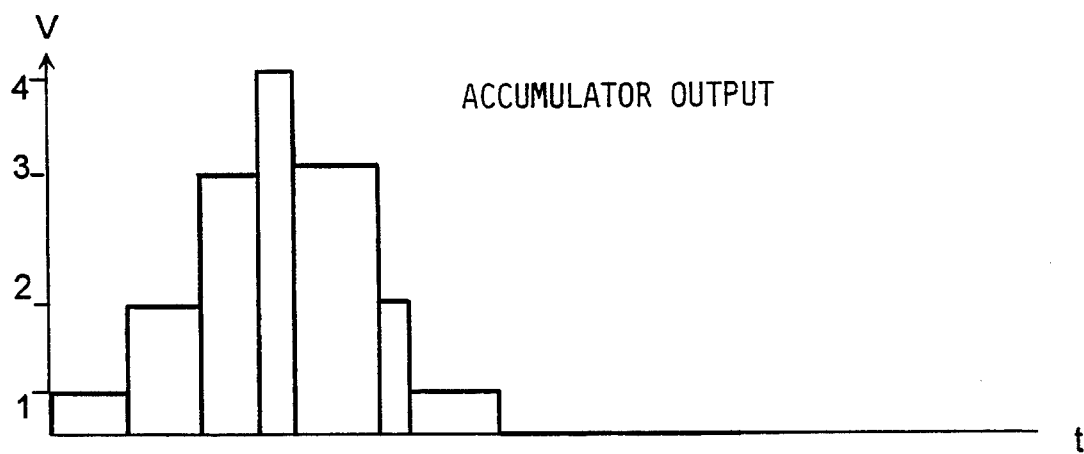
FIG. 20 is a graphical illustration of the level shifted data stored in an accumulator after completion of the steps of the method of flow imaging summarized in FIG. 15 for a region of a vasculature.

The modified echo waveform contained in the accumulator 334 corresponding to the combined level shifted partial modified echo waveforms are graphically depicted in FIG. 20. As a result of the distinct level shifting values applied to the combined signals for each of the distinct filter waveforms W, the data stored in the accumulator 334 for each of the different filter waveforms can be readily distinguished from the data for the other filter waveforms. In the example of image data generated in accordance with the alternative, multiple filter, embodiment shown in FIG. 20, the values stored in the accumulator 334 corresponding to filter waveform $W_1$, have an assigned level 1 value, the waveform values stored in the accumulator 334 corresponding to filter waveform $W_2$, have an assigned level 2 value, etc.

Next, at step 414, the accumulated waveform values graphically depicted in FIG. 20, are transferred to the acoustic frame buffer 112 via switch SW.1 for processing and display in accordance with the afore-described flow imaging processing steps. The signal levels are used to modulate the color of the flow image, or alternatively the intensity of the displayed color. In this manner, the flow image not only displays where flow is occurring, the flow image also displays a map of zones of faster and slower moving blood.

In each of the four filter waveform sequences shown in FIG. 16a, the number of signal samples J remains constant. However, the repetition frequency is increased after each of the first three sampling sequences to provide a total of four signal sample sets characterized by four different signal response curves (schematically displayed in FIG. 13b). The first sampling sequence (1), characterized by a relatively low repetition frequency, provides a peak response at frequency $F_1$ which would be associated with detection of slow moving blood. The second sampling sequence (2), characterized by a higher repetition frequency than sampling sequence (1), provides a peak response at a higher frequency $F_2$ which would be associated with detection of slightly faster moving blood. Sampling sequences (3) and (4), characterized by yet higher repetition frequencies, provide peak responses at frequencies $F_3$ and $F_4$ respectively which detect blood flowing at two higher ranges of speed.

Figure 16B:
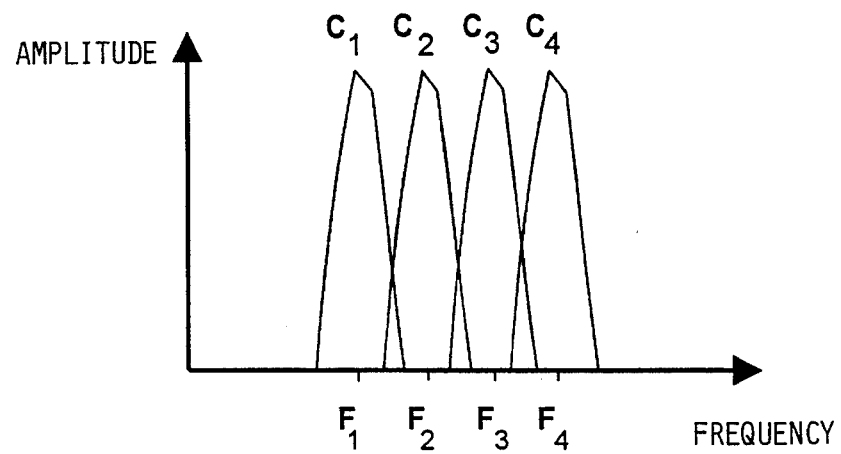
Figure 17:
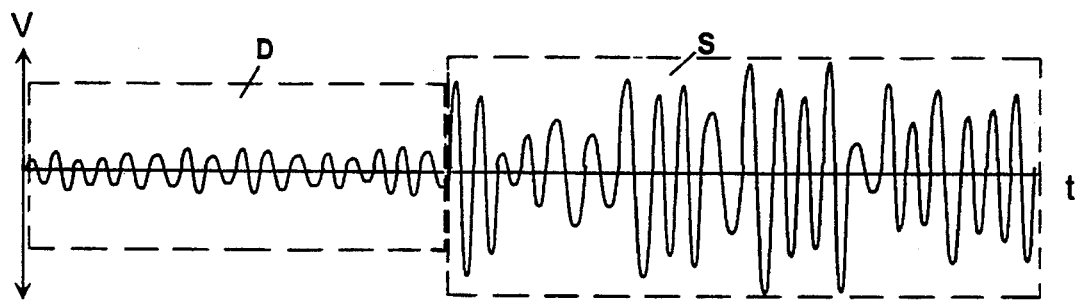
FIG. 17 is an exemplary graphical illustration of an echo signal waveform for a region to be imaged, the waveform having a relatively dynamic portion from echoes caused by the blood and a relatively static portion from echoes caused by the tissue.

Though the response characteristic for a sampling sequence has been described in FIGS. 16a and 16b with respect to modifications to the repetition frequency, it is noted that the response characteristic is also affected by the value of M described herein above. Therefore, modifying the value of M and/or the repetition frequency results in a modified frequency response for an applied filter waveform sequence.

The illustrated alternative embodiment of the flow image processor for producing a multiple filter flow image includes only one set of processing hardware for applying a filter sequence to a set of J signal samples for an image region. As a result, the image processor receives multiple sets of J signal samples for the image region, each one of the filter sequences being applied to a separate one of the multiple sets of J signal samples for the image region. It is considered within the scope of the invention to execute the steps of applying the multiple filter sequences in parallel to a single received set of J signal samples for an image region using a plurality of copies of the hardware schematically depicted in FIG. 13. It is also within the scope of the present invention to serially apply the separate filter sequences to a same set of J signal samples for an image region.

3. Alternative Image Reconstruction Schemes

The illustrated embodiment of the flow image construction technique does not utilize the reconstructive focusing technique utilized in the imaging method set forth in the Proudian et al. '097 patent. When the number of signal samples (J) is large (e.g. 256), the volume of blood responsible for echo signals received by one set of activated transducer elements is not the same as the volume of blood causing echo signals to be received by a next set of activated transducer elements for receiving a next set of J echo signals from another radial section of the imaged region since a substantial period of time has elapsed between the acquisition of the two sets of J signal samples. Therefore, when the value of J is large, performing the complex reconstructive focusing calculations to obtain a flow image is not preferred over the less complex image computation scheme described above for calculating focus points for the flow image.

However, if the selected value of J is small (e.g. 2), then the volume of blood is substantially the same for adjacent transducer echo reception positions. Therefore, in an alternative embodiment of the invention, the reconstructive focusing technique of imaging (described in the Proudian et al. '097 patent) is used to construct a more detailed flow image from image signals obtained from ultrasonic echoes received by the probe assembly over a very short time period.

While the invention has been described in connection with certain preferred and alternative embodiments, there is no intent to limit it to those embodiments. For example, though the present invention is preferably carried out using a probe assembly having a cylindrical array of transducer elements of the general type described in the Proudian et al. U.S. Pat. No. 4,917,097, other suitable probe assemblies known to those skilled in the art are also suitable for carrying out the present invention. These alternative probe assemblies include, for example, rotating transducer probe assemblies having less than a complete transducer array around the diameter of the probe assembly, a single rotating mirror assembly, or a rotating transducer mechanical imaging catheter. Furthermore, the transducer array may be arranged on the front of the probe assembly as a forward viewing imaging device or as a planar surface mounted upon the side of a probe assembly.

Alternative suitable methods and signal processing circuitry for enhancing the signals from non-stationary targets while suppressing the signals from relatively stationary targets are also considered to fall within the scope of the present invention including, for example, the averaging method described by Pasterkamp et al., "Discrimination of the Intravascular Lumen and Dissections in a Single 30 MHz US Image: Use of 'Confounding' Blood Backscatter to Advantage," Radiology, 1993 Vol. 187, No. 3, pp. 871–872, wherein adjacent frames of images are subtracted, and the resultant subtraction images are averaged over a series of 15–25 consecutive frames. Such an averaging scheme could be applied to the DSA 110 of the present invention. However, in accordance with the present invention, this averaging scheme would be implemented in the transduced echo signal domain (either the analog or digitized form) rather than in the image frame domain.

Other hardware configurations are also contemplated. For instance, modulation of the signal samples can be accomplished by hardware before being transferred to the DSA 110. The DSA 110 would then simply perform addition on the modulated signal sample sets. Other methods of subtraction/averaging can be conceived, but it is important that they operate on sets of transduced echo data (rather than pixel image data arising from whole frame images) in the manner described herein in order to overcome the limitations of the prior art.

The scope of the present invention is intended to include, without limitation, any other modifications to the manner of transmitting, receiving, and analyzing the ultrasound signals and the hardware used to carry out the modifications which would be known to those skilled in the art in view of the description of the invention and/or various preferred and alternative embodiments described herein. The intent is to cover all alternatives, modifications and equivalents included within the spirit and scope of the invention as defined by the appended claims.

What is claimed is:

1. A method for constructing an image of a region within a vasculature indicative of blood flow within the region, the method comprising the steps of:

emitting an ultrasonic waveform from within a lumen of the vasculature, the ultrasonic waveform thereafter propagating through the region within the vasculature;

sensing echoes of the emitted ultrasonic waveform arising from reflections of the ultrasonic waveform from tissue and blood within the region;

converting the sensed echoes into an echo waveform;

repeating the emitting, sensing and converting steps a plurality of times to obtain a set of echo waveforms arising from the sensed echoes from the region;

combining the set of echo waveforms to form a modified echo waveform indicating areas within the region occupied by relatively dynamic features, including flowing blood, the portions of the set of echo waveforms arising from relatively static features in the region, including tissue, being substantially attenuated in the modified echo waveform; and processing the modified echo waveform to provide a first image of the region of the vasculature, the first image primarily representing relatively dynamic features in the region.

2. The method of claim 1 wherein the processing step comprises the step of converting the modified echo waveform into an imaging vector comprising a set of image values.

3. The method of claim 2 wherein the processing step further comprises mapping the set of image values into pixel positions on a video display.

4. The method of claim 1 wherein the emitting step comprises emitting by a cylindrical array of transducers the ultrasonic waveform in a direction orthogonal to primary blood flow in the region.

5. The method of claim 1 wherein the step of combining the set of echo waveforms includes applying an alternating polarity modulating sequence to the echo waveforms.

6. The method of claim 5 wherein the step of applying an alternating polarity modulating sequence comprises alternatingly adding and subtracting subsets of the set of echo waveforms.

7. The method of claim 6 further comprising the step of specifying a quantity of echo waveforms contained in each of the subsets of the set of echo waveforms.

8. The method of claim 5 wherein the step of combining the set of echo waveforms includes applying a magnitude modulating sequence to the set of echo waveforms.

9. The method of claim 8 wherein the step of applying a magnitude modulating sequence includes applying a sinusoidal magnitude modulating sequence to the set of echo waveforms.

10. The method of claim 9 wherein the step of applying a magnitude modulating sequence includes applying a Cosine Taper magnitude modulating sequence to the set of echo waveforms.

11. The method of claim 1 further comprising the steps of:

constructing a second image of the region of the vasculature from ultrasound image data obtained by summing a set of echo waveforms arising from reflections of emitted ultrasonic waveforms from tissue and blood within the region, said second image primarily representing relatively static features within the region; and combining the first image and second image in order to obtain a third image that displays in a contrasting manner relatively static features and relatively dynamic features of the region, thereby providing an image of a lumen suitable for medical uses.

12. The method of claim 11 wherein said combining step includes colorizing selected portions of the first image.

13. The method of claim 1 wherein the combining step includes transforming an analog echo waveform arising from the sensed echoes from an analog form into a digitized form.

14. The method of claim 1 wherein a time period between successive repetitions of the emitting and sensing steps for the region is less than a maximum time period in which a second, relatively static, portion of the echo waveform arising from ultrasonic echoes including the ultrasonic echoes from the tissue is distinguishable from a first, relatively dynamic, portion of the echo waveform arising from ultrasonic echoes including the ultrasonic echoes from flowing blood when corresponding portions of successive ones of the set of echo waveforms are compared.

15. The method of claim 14 wherein the period between successive repetitions is less than a thousandth of a second.

16. The method of claim 14 wherein the period between successive repetitions is less than a ten-thousandth of a second.

17. The method of claim 14 wherein the period between successive repetitions is less than a hundred-thousandth of a second.

18. The method of claim 1 wherein the combining step comprises applying a filter sequence to the set of echo waveforms, the filter sequence attenuating relatively static portions of the echo waveforms.

19. The method of claim 1 wherein the combining step comprises applying a plurality of filter sequences to the set of echo waveforms to obtain a plurality of partial modified echo waveforms, each filter sequence providing sensitivity to a range of rate of movement of the blood in the region.

20. The method of claim 19 wherein the combining step further comprises level shifting the partial modified echo waveforms by assigning a distinct level value to each of the plurality of partial modified echo waveforms and combining the level shifted partial modified echo waveforms to obtain the modified echo waveform, the modified echo waveform being indicative of different rates of movement of the blood in the region.

21. The method of claim 20 further comprising the step of assigning a visually distinct display mode to each distinct level value associated with each of the partial modified echo waveforms comprising the modified echo waveform.

22. The method of claim 1 further comprising the steps of:

selecting a new region within a vasculature; and second repeating the emitting, sensing, converting, repeating, combining and processing steps for the new region in order to provide a first image of the new region of the vasculature.

23. The method of claim 22 further comprising the steps of:

reiterating the selecting and second repeating steps a plurality of times in order to provide a first image for a portion of the vasculature in the vicinity of a probe assembly.

24. An ultrasonic imaging system for constructing an image of a region within a vasculature indicative of blood flowing within the region, the ultrasonic imaging system comprising:

a probe assembly including an ultrasound transducer assembly communicatively coupled to an image processing control unit for causing the ultrasound transducer assembly to repeat a plurality of times to obtain a set of echo waveforms:

emitting an ultrasonic waveform from within a lumen of the vasculature, the ultrasonic waveform propagating through the region within the vasculature, sensing echoes of the emitted ultrasonic waveform arising from reflections of the ultrasonic waveform from tissue and blood within the region, and converting the sensed echoes of the emitted ultrasonic waveform into an echo waveform;

an echo waveform processing unit, communicatively coupled to the image processing control unit, for receiving and combining the set of echo waveforms, in accordance with control signals transmitted by the image processing control unit, to form a modified echo waveform indicating areas within the region occupied by relatively dynamic features including flowing blood, the portions of the set of echo waveforms arising from relatively static features in the region, including tissue, being substantially attenuated in the modified echo waveform; and an ultrasound image processor for constructing a first image of the region of the vasculature from the modified echo waveform, the first image primarily representing relatively dynamic features in the region.

25. The ultrasonic imaging system of claim 24 wherein the transducer assembly comprises a cylindrical array of transducers for emitting and receiving ultrasonic waveforms in a direction orthogonal to primary blood flow in the region.

26. The ultrasonic imaging system of claim 24 wherein the echo waveform processing unit includes:

an analog to digital (A/D) converter for receiving the set of echo waveforms and converting the set of echo waveforms from analog form into digital form; and an arithmetic unit communicatively coupled to the A/D converter and the image processing control unit for receiving the set of echo waveforms in digital form and processing the set of echo waveforms in digital form in accordance with an addition/subtraction mode control signal transmitted from the image processing control unit.

27. The ultrasonic imaging system of claim 26 wherein the image processing control unit includes a mode control memory specifying a substantially balanced sequence of addition/subtraction mode control signals to the arithmetic unit for processing the set of echo waveforms in digital form.

28. The ultrasonic imaging system of claim 24 wherein the image processing control unit includes a polarity sequence generator for providing a sequence of polarity control signals to the echo waveform processing unit specifying the manner in which the echo waveform processing unit combines the set of echo waveforms.

29. The ultrasound imaging system of claim 28 wherein the echo waveform processing unit includes an arithmetic unit for adding and subtracting subsets of the set of echo waveforms in accordance with the sequence of polarity control signals.

30. The ultrasonic imaging system of claim 29 wherein the polarity sequence generator specifies a quantity of echo waveforms contained in each of the subsets of the set of echo waveforms.

31. The ultrasonic imaging system of claim 28 wherein the image processing control unit includes a scaling circuit for specifying a set of scaling coefficients for the set of echo waveforms; and wherein the echo waveform processing unit includes a coefficient multiplier for scaling the magnitude of the echo waveforms in accordance with the set of scaling coefficients provided by the scaling circuit.

32. The ultrasonic imaging system of claim 31 wherein the scaling circuit specifies a sinusoidal sequence of scaling coefficients for scaling the set of echo waveforms.

33. The ultrasonic imaging system of claim 32 wherein the scaling circuit further scales the set of echo waveforms by a cosine taper sequence of scaling coefficients.

34. The ultrasound imaging system of claim 24 further comprising means for producing a second image of the region of the vasculature from ultrasound image data obtained by summing a set of echo waveforms arising from reflections of emitted ultrasonic waveforms from tissue and blood within the region, said second image primarily representing relatively static features within the region; and means for combining the first image and second image in order to obtain a third image that displays in a contrasting manner relatively static features and relatively dynamic features of the region, thereby providing an image of a lumen suitable for medical uses.

35. The ultrasound imaging system of claim 34 further comprising means for selectively colorizing portions of the first image indicating relatively dynamic features within the region.

36. The ultrasound imaging system of claim 24 wherein the echo waveform processing unit comprises means for applying a filter sequence to the set of echo waveforms, the filter sequence attenuating relatively static portions of the set of echo waveforms.

37. The ultrasound imaging system of claim 24 wherein the echo waveform processing unit comprises means for applying a plurality of filter sequences to the set of echo waveforms to obtain a plurality of partial modified echo waveforms, each filter sequence providing sensitivity to a range of rate of movement of the blood in the region.

38. The ultrasound imaging system of claim 37 wherein the echo waveform processing unit further comprises a threshold detector/level shifter for assigning a distinct level value to portions of each of the plurality of partial modified echo waveforms meeting a threshold value; and an accumulator for combining the partial modified echo waveforms to obtain the modified echo waveform, the modified echo waveform being indicative of different rates of movement of the blood in the region.

39. The ultrasound imaging system of claim 38 further comprising means for displaying the first image in visually distinct display modes in accordance with each distinct level value for the partial modified echo waveforms comprising the modified echo waveform.

40. The ultrasound imaging system of claim 24 further comprising:

means for selecting a new region within a cross section of the vasculature; and means for controlling the transducer assembly, echo waveform processing unit, and ultrasound image processor to provide a first image for the new region of the vasculature.

41. The ultrasound imaging system of claim 40 further comprising:

means for causing the transducer assembly, echo waveform processing unit, and ultrasound image processor to select a plurality of new regions within the cross section of the vasculature in the vicinity of the probe assembly and provide a first image for each new region.

* * * * *